(12) United States Patent
Lucas et al.

(10) Patent No.: US 7,906,483 B2
(45) Date of Patent: *Mar. 15, 2011

(54) METHOD FOR TREATING TRANSPLANT REJECTION

(75) Inventors: Alexandra Lucas, London (CA); Z. Robert Zhong, London (CA); D. Grant McFadden, London (CA)

(73) Assignee: Viron Therapeutics Inc., London (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/380,063

(22) Filed: Feb. 23, 2009

(65) Prior Publication Data

US 2009/0221472 A1 Sep. 3, 2009

Related U.S. Application Data

(63) Continuation of application No. 10/388,149, filed on Mar. 13, 2003, now Pat. No. 7,514,405, which is a continuation of application No. 09/698,435, filed on Oct. 27, 2000, now abandoned.

(60) Provisional application No. 61/161,643, filed on Oct. 27, 1999.

(51) Int. Cl.
*A61K 38/17* (2006.01)

(52) U.S. Cl. ......................................................... 514/12

(58) Field of Classification Search ........................ None
See application file for complete search history.

(56) References Cited

U.S. PATENT DOCUMENTS

| | | | |
|---|---|---|---|
| 5,686,409 A | 11/1997 | McFadden et al. |
| 5,688,824 A | 11/1997 | Williams |
| 5,917,014 A | 6/1999 | McFadden et al. |
| 5,939,525 A | 8/1999 | McFadden et al. |
| 7,285,530 B2 | 10/2007 | Lucas et al. |
| 7,514,405 B2 | 4/2009 | Lucas et al. |
| 2004/0029801 A1 | 2/2004 | Zhong et al. |

FOREIGN PATENT DOCUMENTS

| | | |
|---|---|---|
| EP | 0356945 B1 | 11/1993 |
| EP | 0567816 A1 | 11/1993 |
| EP | 0985412 A2 | 3/2000 |
| EP | 1365798 | 4/2002 |
| EP | 0817646 B1 | 1/2003 |
| EP | 1223971 B1 | 6/2005 |
| JP | H2-108633 | 4/1990 |
| JP | H6-9425 | 1/1994 |
| WO | WO 91/15221 | 10/1991 |
| WO | WO 92/06706 | 4/1992 |
| WO | WO 92/22320 | 12/1992 |
| WO | WO 93/10812 | 6/1993 |
| WO | WO 95/27503 | 10/1995 |
| WO | WO 96/30042 | 10/1996 |
| WO | WO 97/10006 | 3/1997 |
| WO | WO 99/62540 | 12/1999 |
| WO | WO 00/45834 | 8/2000 |
| WO | WO 00/53793 | 9/2000 |
| WO | WO 01/30379 | 5/2001 |
| WO | WO 01/38790 | 5/2001 |
| WO | WO 01/039790 | 6/2001 |
| WO | WO 02/026245 | 4/2002 |
| WO | WO 2004/039391 | 5/2004 |

OTHER PUBLICATIONS

Aziz et al., "Transplant Arterial Vasculopathy: Evidence for a Dual Pattern of Endothelial Injury and the Source of Smooth Muscle Cells in Lesions of Intimal Hyperplasia," *J. Heart Lung Transplant.* 14:S123-S136, 1995.

Abraham et al., "$\beta_4$-Integrins Mediate Antigen-Induced Late Bronchial Responses and Prolonged Airway Hyperresponsiveness in Sheep," *J. Clin. Invest.* 93:776-787, 1994.

Abraham et al., "Characterization of a Late Phase Pulmonary Response after Antigen Challenge in Allergic Sheep," *Am. Rev. Respir. Dis.* 128:839-844, 1993.

Barsoum, "Introduction of Stable High-Copy-Number DNA into Chinese Hamster Ovary Cells by Electroporation," *DNA Cell. Biol.* 9:293-300, 1990.

Bédard et al., "Prevention of Chronic Renal Allograft Rejection by SERP-1 Protein," *Transplantation* 81:908-914, 2006.

Ben-Nun et al., "The Rapid Isolation of Clonable Antigen-Specific T Lymphocyte Lines Capable of Mediating Autoimmune Encephalomyelitis," *Eur. J. Immunol.* 11:195-199, 1981.

Bowes et al., "Diaspirin Cross-Linked Hemoglobin Improves Neurological Outcome Following Reversible but not Irreversible CNS Ischemia in Rabbits," *Stroke* 25:2253-2257, 1994.

Burgess et al., "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue" *J. Cell Biol.* 111:2129-2138, 1990.

Burkly et al., "Protection Against Adoptive Transfer of Autoimmune Diabetes Mediated Through Very Late Antigen-4 Integrin," *Diabetes* 43:529-534, 1994.

Colvin, "CADI, Canti, Cavi," *Transplantation* 83:677-678, 2007.

Cosimi et al., "In Vivo Effects of Monoclonal Antibody to ICAM-1 (CD54) in Nonhuman Primates with Renal Allografts," *J. Immunol.* 144:4604-4612, 1990. Dai et al., "Serp-1, a Viral Anti-Inflammatory Serpin, Regulates Cellular Serine Proteinase and Serpin Responses to Vascular Injury," *J. Biol. Chem.* 278:18563-18572, 2003.

Davis et al., "The Effect of Age on Cerebral Oedema, Cerebral Infarction and Neuroprotective Potential in Experimental Occlusive Stroke," *Acta Neurochir. Suppl.* 60:282-284, 1994.

(Continued)

*Primary Examiner* — Ilia Ouspenski

(74) *Attorney, Agent, or Firm* — Clark & Elbing LLP; Kristina Bieker-Brady

(57) ABSTRACT

Compositions and methods for treating transplant rejection in a mammalian transplant recipient are provided. The method involves administering a therapeutically effective amount of Serp-1, its analogs, and biologically active fragments thereof in combination with an anti-rejection agent, such as cyclosporin, and a pharmaceutically acceptable carrier to a subject in need of such treatment. The compositions and methods are useful for treating acute and chronic allograft and xenograft transplant rejection in mammals.

109 Claims, 5 Drawing Sheets

OTHER PUBLICATIONS

Davison and Moss, "New Vaccinia Virus Recombination Plasmids Incorporating a Synthetic Late Promoter for High Level Expression of Foreign Proteins," *Nucl. Acids Res.* 18:4285-4286, 1990.

Doerschuk et al., "CD18-Dependent and -Independent Mechanisms of Neutrophil Emigration in the Pulmonary and Systemic Microcirculation of Rabbits," *J. Immunol.* 144:2327-2333, 1990.

Fava et al., "Transforming Growth Factor α1 (TGF- α1) Induced Neutrophil Recruitment to Synovial Tissues: Implications for TGF-α-Driven Synovial Inflammation and Hyperplasia," *J. Exp. Med.* 173:1121-1132, 1991.

Friedrichs et al., "Effects of Heparin and N-Acetyl Heparin on Ischemia/Reperfusion-Induced Alterations in Myocardial Function in the Rabbit Isolated Heart," *Circulation Res.* 75:701-710, 1994.

Fritz, "Proteinase Inhibitors in Severe Inflammatory Processes (Septic Shock and Experimental Endotoxaemia): Biochemical, Pathophysiological and Therapeutic Aspects," in *Protein Degradation in Health and Disease, Ciba Foundation Symposium 75* :351-379, 1980.

Fryer et al., "Influence of Macrophage Depletion on Bacterial Translocation and Rejection in Small Bowel Transplantation," *Transplantation* 62:553-559, 1996.

Gilhar and Elzioni, "The Nude Mouse Model for the Study of Human Skin Disorders," *Dermatology* 189:5-8, 1994.

Gooding et al., "Virus Proteins that Counteract Host Immune Defenses" *Cell* 71:5-7, 1992.

Gown et al., "Human Atherosclerosis- Immunocytochemical Analysis of the Cellular Composition of Human Atherosclerotic Lesions," *Am. J. Physiol.* 125:191-207, 1986.

Haber, "Can a Viral Serine Proteinase Inhibitor Prevent Postangioplasty Restenosis?" *Circulation* 94:2694-2695, 1996.

Hagerty and Allen, "Tolerance to Self and the Processing and Presentation of Self Antigens," *Intern. Rev. Immunol.* 10:313-319, 1993.

Hammer et al., "Spontaneous Inflammatory Disease in Transgenic Rates Expressing HLA-B27 and Human $\beta_2$m: An Animal Model of HLA-B27-Associated Human Disorders," *Cell* 63:1099-1112, 1990.

Harlan et al., "In Vivo Models of Leukocyte Adherence to Endothelium," in *Adhesion: Its Role in Inflammatory Disease*, Harlan et al. (eds.), W.H. Freeman and Co., New York, 1992, p. 117-150.

Hausen et al., "Viral Serine Proteinase Inhibitor (Serp-1) Effectively Decreases the Incidence of Graft Vasculopathy in Heterotopic Heart Allografts," *Transplantation* 72:364-368, 2001.

Häyry et al., "Chronic Allograft Rejection," *Transplantation Proc.* 28;2337-2338, 1996.

Herzum et al., "Coxsackievirus B3 Infection Leads to Cell Death of Cardiac Myocytes," *J. Mol. Cell Cardiol.* 26:907-913, 1994.

Hickey et al., "T-Lymphocyte Entry Into the Central Nervous System," *J. Neurosci. Res.* 28:254-260, 1991.

Hill et al., "Soluble Complement Receptor Type 1 Ameliorates the Local and Remote Organ Injury After Intestinal Ischemia-Reperfusion in the Rat," *J. Immunol.* 149:1723-1728, 1992.

Howie and Helyer, "The Immunology and Pathology of NZB Mice," *Adv. Immunol.* 198:215-266, 1968.

Huber and Pfaeffle, "Differential $Th_1$ and $Th_2$ Cell Responses in Male and Female BALB/c Mice Infected with Coxsackievirus Group B Type 3," *J. Virology* 68:5126-5132, 1994.

Jiang and Kanost, "Characterization and Functional Analysis of 12 Naturally Occurring Reactive Site Variants of Serpin-1 from *Manduca Sexta*," *J. Biol. Chem.* 272:1082-1087, 1997.

Jiang et al., "Induction of Indefinite Cardiac Allograft Survival Correlates with Toll-Like Receptor 2 and 4 Downregulation after Serine Protease Inhibitor-1 (SERP-1) Treatment," *Transplantation* 84:1158-1167, 2007.

Johnstone et al., "Effects of Intraoperative Radiotherapy on Vascular Grafts in a Canine Model," *Int. J. Radiat. Oncol. Biol. Phys.* 29:1015-1025, 1994.

Kasahara et al., "Autoimmune Myocarditis Induced in Mice by Cardiac C-Protein- Cloning of Complementary DNA Encoding Murine Cardiac C-Protein and Partial Characterization of the Antigenic Peptides," *J. Clin. Invest.* 94:1026-1036, 1994.

Kavanagh et al., "High-Current Stimuli to the Spared Epicardium of a Large Infarct Induce Ventricular Tachycardia," *Circulation* 85:680-698, 1992.

Keelan et al., "Effect of External Abdominal Irradiation on Intestinal Morphology and Brush Border Membrane Enzyme and Lipid Composition," *Radiation Res.* 105:84-96, 1986.

Kelly et al., "Antibody to Intercellular Adhesion Molecule 1 Protects the Kidney Against Ischemic Injury," *Proc. Natl. Acad. Sci. U.S.A.* 91:812-816, 1994.

Kiberd and Young, "Modulation of Glomerular Structure and Function in Murine Lupus Nephritis by Methylprednisolone and Cyclophosphamide," *J. Lab. Clin. Med.* 124:496-506, 1994.

Klinkert et al., "Surface Proteins of *Mycoplasma hyopneumoniae* Identified from an *Escherichia coli* Expression Plasmid Library," *Infect. Immunity* 49:329-335, 1985.

Kodama et al., "Rat Dilated Cardiomyopathy After Autoimmune Giant Cell Myocarditis," *Circ. Res.* 75:278-284, 1994.

Kouwenhoven et al., "Etiology and Pathophysiology of Chronic Transplant Dysfunction," *Transplant Int.* 13:385-401, 2000.

Kung et al., "Characterization of a Murine Model of Allergic Pulmonary Inflammation," *Int. Arch. Allergy Immunol.* 105:83-90, 1994.

Kusumoto et al., "Role of Endogenous Endothelin in Extension of Rabbit Myocardial Infarction," *J. Cardiovasc. Pharmacol.* 22:S339-S342, 1993.

LeDuc and Nast, "Chemotactic Peptide-Induced Acute Colitis in Rabbits," *Gastroenterology* 98:929-935, 1990.

Libby et al., "A Cascade Model for Restenosis—A Special Case of Atherosclerosis Progression," *Circulation* 86(Suppl. 3):47-52, 1992.

Liu et al., "A Novel Viral Anti-Inflammatory Protein, SERP-1, Reduces Intimal Hyperplasia in Cholesterol-Fed Rabbits After Balloon Angioplasty," *Circulation* 88:181, 1993. Abstract 0420.

Lomas et al., "Inhibition of Plasmin, Urokinase, Tissue Plasminogen Activator, and $C_{1s}$ by a Myxoma Virus Serine Proteinase Inhibitor," *J. Biol. Chem.* 268:516-521, 1993.

Lowrance et al., "Spontaneous Elaboration of Transforming Growth Factor β Suppresses Host Defense Against Bacterial Infection in Autoimmune MRL/lpr Mice," *J. Exp. Med.* 180:1693-1703, 1994.

Lucas et al., "Transplant Vasculopathy: Viral Anti-Inflammatory Serpin Regulation of Atherogenesis," *J. Heart Lung Transplant.* 19:1029-1038, 2000.

Lucas et al., "Virus-Encoded Serine Proteinase Inhibitor SERP-1 Inhibits Atherosclerotic Plaque Development After Balloon Angioplasty," *Circulation* 94:2890-2900, 1996.

Lucas et al., "A Unique Viral Anti-Inflammatory Protein, SERP-1, Reduces Intimal Hyperplasia in Cholesterol-Red Rabits After Angioplasty," J. Cell. Biochem. Suppl. 18A:286, 1994. Abstract E 315.

Macen et al., "SERP1, a Serine Proteinase Inhibitor Encoded by Myxoma Virus, is a Secreted Glycoprotein that Interferes with Inflammation," *Virology* 195:348-363, 1993.

Maksymowych et al., "Amelioration of Established Antigen-Induced Arthritis in Rabbits Treated with a Secreted Viral Serine Proteinase Inhibitor," *J. Rheumatol.* 23:878-882, 1996.

Martorana et al., "Antiischemic Effects of Pirsidomine, a New Nitric Oxide Donor," *Eur. J. Pharmacol.* 257:267-273, 1994.

Mathison et al., "Platelet Activating Factor and Systemic Anaphylasix in *Nippostrongylus brasiliensis*-Sensitized Rats: Differential Effects of PAF Antagonists," *Br. J. Pharamcol.* 106:263-266, 1992.

Mazur et al., "Selective $\alpha_{11b}\beta_3$ Receptor Blockage with Peptide TP9201 Prevents Platelet Uptake on Dacron Vascular Grafts Without Significant Effect on Bleeding Time," *J. Lab. Clin. Med.* 124:589-599, 1994.

McCune et al., "Immunosuppressive Drug Therapy for Rheumatic Disease," *Curr. Opin. Rheumatol.* 5:282-292, 1993.

McFadden et al., "Interruption of Cytokine Networks by Poxviruses: Lessons from Myxoma Virus," *J. Leukocyte Biol.* 57:731-738, 1995.

McFadden and Graham, "Modulation of Cytokine Networks by Poxvirus: the Myxoma Virus Model," *Virology* 5:421-429, 1994.

McFadden, "Rabbit, Hare, Squirrel and Swine Poxviruses" in *Encyclopedia of Virology*, Webster et al. (eds.), Academic Press, San Diego, CA, 1994, p. 1153-1160.

McFadden, "DNA Viruses that Affect Cytokine Networks," in *Human Cytokines: Their Role in Disease and Therapy*, Aggarwal et al. (eds.), Blackwell Scientific, Cambridge, MA, p. 401-420.

Merck Research Laboratories, *The Merck Manual of Diagnosis and Therapy* (17th Edition), pp. 1072-1073, 1999.

Mihelcic et al., "Inhibition of Leukocyte L-Selectin Function With a Monoclonal Antibody Attenuates Reperfusion Injury to the Rabbit Ear," *Blood* 84:2322-2328, 1994.

Mikayama et al., "Molecular Cloning and Functional Expression of a cDNA Encoding Glycosylation-Inhibiting Factor," *Proc. Natl. Acad. Sci. U.S.A.* 90:10056-10060, 1993.

Miller et al., "Introduction: Allograft Coronary Disease," *J. Heart Lung Transplant* 14:S109-S110, 1995.

Miller et al., "Specific Interaction of Lymphocyte Function-Associated Antigen 3 with CD2 Can Inhibit T Cell Responses," *J. Exp. Med.* 178:211-222, 1993.

Miller et al., "Inhibition of Transplant Vasculopathy in Rat Aortic Allograft Model After Infusion of Anti-Inflammatory Viral Serpin," *Circulation* 101:1598-1605, 2000.

Mossman et al., "The Myxoma Virus-Soluble Interferon-γ Receptor Homolog, M-T7, Inhibits Interferon-γ in a Species-Specific Manner," *J. Biol. Chem.* 270:3031-3038, 1995.

Mossman et al., "Myxoma Virus M-T7, a Secreted Homolog of the Interferon-Gamma Receptor, Is a Critical Virulence Factor for the Development of Myxomatosis in European Rabbits," *Virology* 215:17-30, 1996.

Mulligan et al., "Role of Leukocyte Adhesion Molecules in Lung and Dermal Vascular Injury After Thermal Trauma of Skin," *Am. J. Pathol.* 144:1008-1015, 1994.

Mulligan et al., "Role of $\beta_1$, $\beta_2$ Integrins and ICAM-1 in Lung Injury After Deposition of IgG and IgA Immune Complexes," *J. Immunol.* 150:2407-2417, 1993.

Mulligan et al., "Role of Leukocyte Adhesion Molecules in Complement-Induced Lung Injury," *J. Immunol.* 150:2401-2406, 1993.

Mulligan et al., "Protective Effects of Soluble CR1 in Complement- and Neutrophil-Mediated Tissue Injury," *J. Immunol.* 148:1479-1485, 1992.

Nakamoto et al., "In Vivo Treatment of Infected Prosthetic Graft Material with Urokinase: An Animal Model," *J. Vasc. Interv. Radiol.* 5:549-552, 1994.

Nash et al., "SERP-1, a Poxvirus-Encoded Serpin, is Expressed as a Secreted Glycoprotein that Inhibits the Inflammatory Response to Myxoma Virus Infection," *Adv. Exp. Med. Biol.* 425:195-205, 1997.

Nash et al., "Inhibitory Specificity of the Anti-Inflammatory Myxoma Virus Serpin, SERP-1," *J. Biol. Chem.* 273:20982-20991, 1998.

Nicoletti et al., "The Effects of Thymopentin on the Development of SLE-Like Syndrome in the MRL/lpr-lpr Mouse," *Scand. J. Immunol.* 40:549-556, 1994.

Office Action for U.S. Appl. No. 10/388,149, mailed on Jun. 17, 2005.

Office Action for U.S. Appl. No. 10/388,149, mailed on Dec. 23, 2005.

Office Action for U.S. Appl. No. 10/388,149, mailed on Jul. 6, 2006.

Office Action for U.S. Appl. No. 10/388,149, mailed on Sep. 14, 2007.

Okuda et al., "Elevated Expression of Transforming Growth Factor-β and Proteoglycan Production in Experimental Glomerulonephritis," *J. Clin. Invest.* 86:453-462, 1990.

Paul et al., "The Efficacy of LFA-1 and VLA-4 Antibody Treatment in Rat Vascularized Cardiac Allograft Rejection," *Transplantation* 55:1196-1199, 1993.

Paul et al., "Macrophage Subpopulations in Normal and Transplanted Heart and Kidney Tissues in the Rat," *Transplantation* 53:157-162, 1992.

Pemberton et al., "Microvascular Effects of Complement Blockade with Soluble Recombinant CR1 on Ischemia/Reperfusion Injury of Skeletal Muscle," *J. Immunol.* 150:5104-5113, 1993.

Penning et al.,"The Design and Synthesis of Second Generation Leukotriene $B_4$ ($LTB_4$) Receptor Antagonists Related to SC-41930," *Agents Actions* 39:C11-C13, 1993.

Percy et al., "In Vitro Changes in the Properties of Rabbit Colonic Muscularis Mucosae in Colitis," *Gastroenterology* 104:369-376, 1993.

Peterseim et al., "Stability of the β-Adrenergic Receptor/Adenylyl Cyclase Pathway of Pediatric Myocardium after Brain Death," *J. Heart Lung Transplant.* 13:635-640, 1994.

Podolsky et al., "Attenuation of Colitis in the Cotton-Top Tamarin by Anti-α4 Integrin Monoclonal Antibody," *J. Clin. Invest.* 92:372-380, 1993.

Popovich et al., "Elevation of the Neurotoxin Quinolinic Acid Occurs Following Spinal Cord Trauma," *Brain Res.* 633:348-352, 1994.

Popovich et al., "Differential Expression of MHC Class II Antigen in the Contused Rat Spinal Cord," *J. Neurotrauma* 10:37-46, 1993.

Pretolani et al., "Antibody to Very Late Activation Antigen 4 Prevents Antigen-Induced Bronchial Hyperreactivity and Cellular Infiltration in the Guinea Pig Airways," *J. Exp. Med.* 180:795-805, 1994.

Rabb et al., "The Role of the Leukocyte Adhesion Molecules VLA-4, LFA-1, and Mac-1 in Allergic Airway Response in the Rat," *Am. J. Respir. Crit. Care Med.* 149:1186-1191, 1994.

Rabinovici et al.,"Role of Complement in Endotoxin/Platelet-Activating Factor-Induced Lung Injury," *J. Immunol.* 149:1744-1750, 1992.

Ramaswamy et al., "Pathology of Pulmonary Parasitic Migration: Morphological and Bronchoalveolar Cellular Responses Following *Nippostrongylus brasiliensis* Infection in Rats," *J. Parasitol.* 77:302-312, 1991.

Ramos et al., "Difrerences in Non-MHC Alloantigens Promote Tissue Rejection but Fail to Mediate Allogeneic Co-operation and Autoimmunity in Mice Neonatally Injected with Semi-Allogeneic $F_1$ B Cells," *Immunology* 82:287-293, 1994.

Ramzy et al., "Cardiac Allograft Vasculopathy: A Review," *Can. J. Surg.* 48:319-327, 2005.

Remaut et al., "Plasmid Vectors for High-Efficiency Expression Controlled by the $_{pL}$ Promoter of Coliphage Lambda," *Gene* 15:81-93, 1981.

Santing et al., "Dissociation Between Bronchial Hyperreactivity In Vivo and Reduced β-Adrenoceptor Sensitivity In Vitro in Allergen-Challenged Guinea Pigs," *Eur. J. Pharm.* 257:145-152, 1994.

Santoian et al., "Use of the Porous Balloon in Porcine Coronary Arteries: Rationale for Low Pressure and Volume Delivery," *Cath. Cardiovasc. Diag.* 30:348-354, 1993.

Scott et al., "Local Delivery of an Antithrombin Inhibits Platelet-Dependent Thrombosis," *Circulation* 90:1951-1955, 1994.

Shandelya et al., "Soluble Complement Receptor Type 1 Inhibits the Complement Pathway and Prevents Contractile Failure in the Postischemic Heart," *Circulation* 88:2812-2826, 1993.

Singh and Lebedeva, "Interleukin-1 Contributes to High Level IgG Production in the Murine MRL/lpr Lupus Model," *Immunol. Invest.* 23:281-292, 1994.

Smith, "Virus Strategies for Evasion of the Host Response to Infection," *Trends Microbiol.* 2:81-88, 1994.

Stadius et al., "Local Infusion Balloon Angioplasty to Obviate Restenosis Compared with Conventional Balloon Angioplasty in an Experimental Model of Atherosclerosis," *Am. Heart J.* 126:47-56, 1993.

Strober and Ehrhardt, "Chronic Intestinal Inflammation: An Unexpected Outcome in Cytokine or T Cell Receptor Mutant Mice," *Cell* 75:203-205, 1993.

Strom and Suthanthiran, "Therapeutic Approach to Organ Transplantation," *Therapeutic Immunology*, Blackwell Scientific, Cambridge, MA, pp. 451-456, 1996.

Stokes et al., "An Electromechanical Spinal Injury Technique with Dynamic Sensitivity," *J. Neurotrauma* 9:187-195, 1992.

Sun et al., "Cardiac Angiotensin Converting Enzyme and Myocardial Fibrosis in the Rat," *Cardiovasc. Res.* 28:1423-1432, 1994.

Sunberg et al., "Full-Thickness Skin Grafts from Flaky Skin Mice to Nude Mice: Maintenance of the Psoriasiform Phenotype," *J. Invest. Dermatol.* 102:781-788, 1994.

Tanaka et al., "An Angiotensin II Receptor Antagonist Reduces Myocardial Damage in an Animal Model of Myocarditis," *Circulation* 90:2051-2055, 1994.

Takahashi et al., "In Vivo Differentiation of Edematous Changes After Stroke in Spontaneously Hypertensive Rats Using Differentiation Weighted MRI," *Acta Neurochir. Suppl.* 60:224-227, 1994.

Teerlink et al., "Role of Endothelin in the Maintenance of Blood Pressure in Conscious Rats with Chronic Heart Failure. Acute Effects of the Endothelin Receptor Antagonist Ro 47-0203 (Bosentan)," *Circulation* 90:2510-2518, 1994.

Theofilopoulos and Dixon, "Murine Models of Systemic Lupus Erythematosus," *Adv. Immunol.* 37:269-390, 1985.

Thomas et al., "Role of Leukocyte CD11/CD18 Complex in Endotoxic and Septic Shock in Rabbits," *J. Appl. Physiol.* 73:1510-1516, 1992.

Tilney, "Thoughts on the Immunobiology of Chronic Allograft Rejection," *Transplantation Proc.* 27:2123-2125, 1995.

Tilney et al., "Serial Analysis of Cytokines, Adhesion Molecule Expression, and Humoral Responses During Development of Chronic Kidney Allograft Rejection in a New Rat Model," *Transplantation Proc.* 25:861-862, 1993.

Tilney et al., "Chronic Rejection—An Undefined Conundrum," *Transplantation* 52:389-398, 1991.

Turner et al., "Poxvirus Serpins," *Viroceptors, Virokines and Related Immune Modulators Encoded by DNA Viruses*, G. McFadden (ed.), R.G. Landes Company, Georgetown, Texas, 1994, p. 67-88.

Upton et al., "Myxoma Virus and Malignant Rabbit Fibroma Virus Encode a Serpin-Like Protein Important for Virus Virulence," *Virology* 179:618-631, 1990.

Upton and McFadden, "DNA Sequence Homology Between the Terminal Inverted Repeats of Shope Fibroma Virus and an Endogenous Cellular Plasmid Species," *Mol. Cell. Biol.* 6:265-276, 1986.

Upton et al., "A Novel Member of the Serpin Superfamily is Encoded on a Circular Plasmid-Like DNA Species Isolated from Rabbit Cells," *F.E.B.S. Lett.* 207:115-120, 1986.

Uretsky et al., "Development of Coronary Artery Disease in Cardiac Transplant Patients Receiving Immunosuppressive Therapy with Cyclosporine and Prednisone," *Circulation* 76:827-834, 1987.

Vasquez-Martul et al., "Histological Features with Clinical Impact in Chronic Allograft Nephropathy: Review of 66 Cases," *Transplantation Proceed.* 36:770-771, 2004.

Viswanathan et al., "Serp-1, A Viral Anti-Inflammatory Serpin Alters Gene Expression Profiles in Human Monocytes and Endothelial Cells," *Inflamm. Res.* 52(Suppl. 2):S92, 2003. Abstract 6.3.

Wang et al., "Treatment with a Short Course of LF 15-0195 and Continuous Cyclosporin A Attenuates Acute Xenograft Rejection in a Rat-to-Mouse Cardiac Transplantation Model," *Xenotransplantation* 10:325-336, 2003.

Wang et al., "Serp-1, a Viral Anti-Inflammatory Serpin, Attenuates Acute Xenograft Rejection in a Rat-to-Mouse Cardiac Transplant Model," *Xenotransplantation* 10:506, 2003. Abstract S14.7.

Wilson et al., "The Effect of Low Molecular Weight Heparin on Intimal Hyperplasia in Vein Grafts," *Eur. J. Vasc. Surg.* 8:60-64, 1994.

Wishart et al., "Comparisons of Repetitive- and Single-Insult Ischaemia: Effects on Regional Brain Damage and Behaviour," *NeuroReport* 5:1541-1544, 1994.

Witkowski et al., "In Vivo Estimation of Cardiac Transmembrane Current," *Circ. Res.* 72:424-439, 1993.

Wolinsky et al., "Use of a Perforated Balloon Catheter to Deliver Concentrated Heparin into the Wall of the Normal Canine Artery," *J. Am. Coll. Cardiol.* 15:475-481, 1990.

Yang et al., "Inhibition of Insulitis and Prevention of Diabetes in Nonobese Diabetic Mice by Blocking L-Selectin and Very Late Antigen 4 Adhesion Receptors," *Proc. Natl. Acad. Sci. U.S.A.* 90:10494-10498, 1993.

Yanos et al., "Mechanism of Respiratory Arrest in an Animal Model of Acute Fatal Bronchoconstriction," *J. Appl. Physiol.* 77:236-244, 1994.

Yednock et al., "Prevention of Experimental Autoimmune Encephalomyelitis by Antibodies Against α4β1 Integrin," *Nature* 356:63-66, 1992.

Zamvil et al., "'Lupus-Prone' Mice are Susceptible to Organ-Specific Autoimmune Disease, Experimental Allergic Encephalomyelitis," *Pathobiology* 62:113-119, 1994.

Zhang et al., "Characterization of a Murine Model of Myocarditis Induced by a Reactivated Coxsackievirus B3," *Int. J. Exp. Path.* 75:99-110, 1994.

Zierhut et al., "Pharmacological Actions of SDZ 218-135, A Novel Positive Inotropic Agent," *Cardiovasc. Drugs Ther.* 8:235-244, 1994.

International Search Report for WO 96/30042 dated Sep. 23, 1996.

International Search Report for WO 01/39790 dated Mar. 22, 2001.

International Search Report for WO 01/30379 dated Apr. 12, 2001.

International Search Report for WO 02/026245 dated Jan. 23, 2003.

International Search Report for WO 04/039391 dated Mar. 8, 2004.

Kumano and Endo, "Cyclosporin (Neoral)," *Urol. Surg.* 10:313, 1997 (English abstract only).

Mennander et al, "Chronic Rejection of Rat Aortic Allograft: II. Administration of Cyclosporin Induces Accelerated Allograft Arteriosclerosis," *Transpl. Int.* 4:173-179, 1991.

Yilmaz et al, "Chronic Rejection of Rat Renal Allograft: I. Histological Differentiation between Chronic Rejection and Cyclosporin Nephrotoxicity," *Transpl. Int.* 5:85-95, 1992.

METHOD FOR TREATING TRANSPLANT REJECTION

CROSS-REFERENCE TO RELATED APPLICATIONS

This application is a continuation of U.S. application Ser. No. 10/388,149 filed on Mar. 13, 2003 now U.S. Pat No. 7,514,405, which is a continuation of U.S. application Ser. No. 09/698,435, filed Oct. 27, 2000 now abandoned, which claims the benefit of the filing date of U.S. Provisional Application No. 60/161,643, filed Oct. 27, 1999.

FIELD OF THE INVENTION

The present invention relates to the use of a viral protein, Serp-1, and its analogs, and biologically active fragments thereof in combination with an anti-rejection agent to treat acute and chronic transplant rejection in mammals.

BACKGROUND OF THE INVENTION

The success of surgical transplantation of organs and tissue is largely dependent on the ability of the clinician to modulate the immune response of the transplant recipient.

Specifically, the immunological response directed against the transplanted foreign tissue must be controlled if the tissue is to survive and function. It is known that the normally functioning immune system of the transplant recipient recognizes the transplanted organ as "non-self" tissue and thereafter mounts an immune response to the presence of the transplanted organ. Left unchecked, the immune response will generate a multitude of cells and proteins that will ultimately result in loss of biological functioning or death of the transplanted organ.

Transplant rejection remains the leading impediment to long term graft survival in humans.

Current immunosuppressive therapy used to treat rejection reactions suppresses T and B cell activity but does not alter the inflammatory responses that are believed to contribute to transplant rejection (Fryer et al. (1996) Transplantation 62(5) 553-559).

Tissue and organ transplant recipients are generally treated with one or more cytotoxic agents in an effort to suppress the transplant recipient's immune-response against the transplanted organ or tissue. For example, cyclosporin A (e.g., Neoral® or Sandimmune®), a cyclic peptide consisting of 11 amino acid residues and produced by the fungus species. *Tolypocladium Inflatum Gams*, is currently used to administer to the recipients of kidney, liver, pancreas and heart allografts (i.e., wherein donor and recipient are of the same species). However, administration of cyclosporin A is not without drawbacks as the drug can cause kidney and liver toxicity as well as hypertension. Moreover, the use of cyclosporin A can lead to malignancies (such as lymphoma) and lead to opportunistic infection due to the systemic immunosuppression it induces in patients receiving long, term treatment with the drug, i.e., the normal protective immune response of the host to pathogenic microorganisms is downregulated thereby increasing the risk of infections caused by such microorganisms.

Currently available immunosuppressive agents such as cyclosporin A fail to prevent either acute or chronic refractory rejection. Nearly 20% of cadaver kidney and cardiac grafts are lost during the first year post-transplant, primarily due to acute rejection (Uretsky et al. (1987) *Circulation* 76:827-834; Hosenpud et al. (1994) *Transplantation* 13:561-570; *Canadian Organ Replacement register* 1993 report p. 187; Cook et al. (1987) *Clinical Transplants* 277-285). Chronic rejection poses formidable hurdles for ektant immunosuppressant therapies. 50% of lung transplant recipients develop bronchitis obliterans, the hallmark of chronic ailograft rejection (Miller, L. (1995) *J. Heart Lung Transplant* 14:S109-S110; vonWillebrand et al. (1997) *Transplantation Proc.* 29:1530-1531; Hayry et al. (1996) *Transplantation Proc.* 28:2337-2338; Tilney et al. (1995) *Transplantation Proc.* 27:2123-2125; Tilney et al. (1991) *Transplantation. Proc.* 52:389-398). Only 20% of cadaver renal transplants continue to function at ten years post-transplant (Uretsky et al. (1987) *Circulation* 76:827-834; Hosenpud et al. (1994) Transplantation 13:561-570; *Canadian Organ Replacement register* 1993 report p. 187; Cook et al.

(1987) *Clinical Transplants* 277-285). Transplant vasculopathy, induced by chronic rejection and ischemia, is the leading cause of cardiac transplant graft loss after the first year post transplant (Miller, L. (1995) *J. Heart Lung Transplant* 14:S109-S110). Moreover, current post-transplantation therapy requires continuous (e.g. daily) administration of an anti-rejection agent for the duration of the transplant recipient's life.

Although acute rejection is mainly T-cell activated, the role of inflammation has been recently implicated in the pathogenesis of rejection (Hayry et al. (1996) *Transplantation Proc.* 28:2337-2338). Activation of many cytokines (e.g. IL-2, IFNγ, TNFα) and chemokines (e.g. RANTES, IL-8, MCP-1 and MIP-1α) occurs during inflammatory responses to graft rejection (Hayry et al. (1997) *Transplantation Proc:* 29:2551; vonWillebrand et al. (1997) *Transplantation Proc.* 29:1530-1531; Tilney et al. (1993) 25:861-862). It is believed that decreasing initial inflammation may lead to lower acute and long term rejection rates and improved graft function (Fryer et al. (1996) *Transplantation* 62(5)553-559).

Chronic rejection is less well understood. Historically, chronic vascular rejection has been described as repetitive endothelial injury leading to intimal proliferation, hypertrophy and subsequent luminal occlusion (Tilney et al. (1995) *Transplantation. Proc.* 27:2123-2125; Tilney et al. (1991) *Transplantation Proc.* 52:389-398). Some researchers have proposed inflammatory, humoral, cellular, and cytokine-related non-specific scarring mechanisms as etiologies of chronic rejection (Hayry et al. (1996) *Transplantation Proc.* 28:2337-2338; Tilney et al. (1995) *Transplantation Proc.* 27:2123-2125; Tilney et al. (1991) *Transplantation Proc.* 52:389-398) It is now known that alloantigen-independent factors play an essential role in chronic rejection. For example, human kidney grafts from identical twins lose their grafts at ten years (Tilney et al., (1986) *World J. Surgery.* 10:381-388; Glassock et al.

(1968) *Medicine* 47:411-454). These isograft losses are believed to be a consequence of injury during preservation and reperfusion. Injury from multiple etiologies activates thrombotic and inflammatory cascades in the vascular wall that converge, initiating a rapid pervasive response which stimulates cellular migration, invasion and proliferation at sites of vessel injury (Aziz et al. (1995) *Lung Transplant* 14:S123-S136; Libby et al., (1992) *Circulation* 86:Supp:III: 47-52). As a result, inflammatory mediators and cytokines are upregulated and secreted in response to endothelial injury, which results in the accumulation of macrophages that, in turn, upregulate more chemokines (e.g. RANTES, IL-8, MCP-1 and MIP-1α) (vonWillebrand et al. (1997) *Transplantation Proc.* 29:1530-1531), cytokines (e.g. IL-1, IL-6, TNFα) (Tilney et al. (1993) 25:861-862), and growth factors (Hayry et al. (1997) *Transplantation Proc.* 29:2551).

Large DNA viruses have evolved multiple, highly effective mechanisms over millions of years which enhance, or inhibit the thrombotic/thrombolytic and inflammatory-cascades and alter cellular invasion into areas of tissue injury (Gooding, et al. (1992) *Cell*, 667:141-150; Spriggs, M. K. (1996) *Annu. Rev. Immunol*, 14:101-130; Smith G. L. (1994) *Trends Microbiol.*, 82:80-88). Both the thrombotic/thrombolytic serine proteinases and the inflammatory cytokine cascades have been recently demonstrated to stimulate cellular chemotaxis and mitogenesis (Blasi, F (1997) *Trends in Immunol. Today*, 18:415-419; Luster, A. D. (1998) *N. Eng. Journal*, 338:436-445). The proteins secreted by myxoma virus frequently mimic cellular immune molecules such as cytokine receptors and function by binding and inhibiting cytokines and chemokines or other regulatory proteins (McFadden, et al. (1995) *Leukocyte Biol.*, 57:731-738; Mossman, et al. (1995) *J. Biol. Chem.*, 270:3031-3038). We have previously reported that Serp-1, a serine proteinase inhibitor, inhibits inflammation and atheroma development in rabbit and rat models after balloon injury and dramatically reduces macrophage invasion and atherosclerotic plaque growth in cholesterol fed rabbits after angioplasty injury (Lucas, et al. (1996) *Circulation*, 94:2890-2900). Preliminary studies in a rat aortic allograft model have also demonstrated significant reductions both in mononuclear cell invasion and transplant vasculopathy after infusion of these viral proteins (Miller, et al. (2000) *Circulation*, 101: 1598-1605; Mossman, et al. (1996) *Virology*, 215: 17-30).

Serp-1 is a55 kD glycoprotein that inhibits a variety of serine proteinases that regulate the inflammatory response. Serp-1 regulates thrombolytic proteins, plasmin, tissue plasminogen activator (tPA) and urokinase. A single local infusion of Serp-1 protein, cloned and expressed from a vaccinia vector, at the site of balloon injury dramatically decreases subsequent plaque growth and macrophage invasion (Lucas, et al. (1996) sura). Serp-1 modulates transcription of elements of the thrombolytic cascade soon after endothelial injury. Serp-1 is the subject of three U.S. Pat. Nos. 5,686,409, entitled "Antirestenosis Protein"; and 5,919,014 and 5,939,525 both entitled "Methods of Treating Inflammation and Compositions Therefor."

It has been discovered in accordance with the present invention that co-administration of Serp-1, Serp-1 analogs and biologically active fragments thereof and an anti-rejection agent are capable of preventing allograft and xenograft transplant, rejection in mammals without the need for sustained administration of an anti-rejection agent.

SUMMARY OF THE INVENTION

In accordance with the present invention, it has been surprisingly discovered that co-administration of Serp-1, its analogs and biologically active fragments thereof, and an anti-rejection agent treats allograft and xenograft transplant rejection in animals, including humans. It has also been surprisingly discovered in accordance with the present invention that co-administration of Serp-1 and an anti-rejection agent for a period of about 1 to about 30 days post-transplantation is effective to treat graft rejection without further administration of an anti-rejection agent. In a preferred embodiment co-administration of Serp-1 and an anti-rejection agent is for a period of about 8 to about days post-transplantation.

The present invention provides a method for treating graft rejection in mammals. Graft rejection treatable in accordance with the present invention includes allograft and xenograft transplanted organs. In accordance with the present invention, Serp-1, Serp-1 analogs or biologically active fragments thereof, are co-administered with an anti-rejection agent to a subject in need of such treatment for a time and under conditions sufficient to treat graft rejection.

One embodiment of the invention is directed to treating mammalian kidney transplant rejection. Another embodiment of the invention is directed to treating mammalian heart transplant rejection. Still another embodiment of the invention is directed to treating graft rejection of an organ transplanted from one mammalian species to another, distinct mammalian species. In these embodiments of the invention, the Serp-1, Serp-1 analog or biologically active fragment thereof is delivered together with an anti-rejection agent e.g., Cyclosporin A in a manner consistent with conventional methodologies associated with transplantation of mammalian organs in order to treat graft rejection.

In another embodiment of the present invention, pharmaceutical compositions are provided which include Serp-1, its analogs or biologically fragments thereof and an anti-rejection agent, both of which are admixed with a pharmaceutically acceptable carrier.

These and other objects of the invention are accomplished by the co-administration of Serp-1, its analogs and biologically active fragments thereof in amounts sufficient to achieve the desired therapeutic effect.

BRIEF DESCRIPTION OF THE DRAWINGS

FIG. 2(A) shows a representative renal allograft treated with CsA alone showing typical intimal thickening in an arteriole;

FIG. 2(B) shows a representative renal allograft treated with CsA and a short course of Serp-1 (high dose) showing normal appearance of an arteriole;

FIG. 2(C) shows a representative renali allograft treated with CsA alone, showing typical scarring in a glomerule;

FIG. 2(D) shows a representative renal allograft treated with CSA and a short course of Serp-1 (high dose) showing normal architecture of a glomerule.

DETAILED DESCRIPTION OF THE INVENTION

Figure 1:
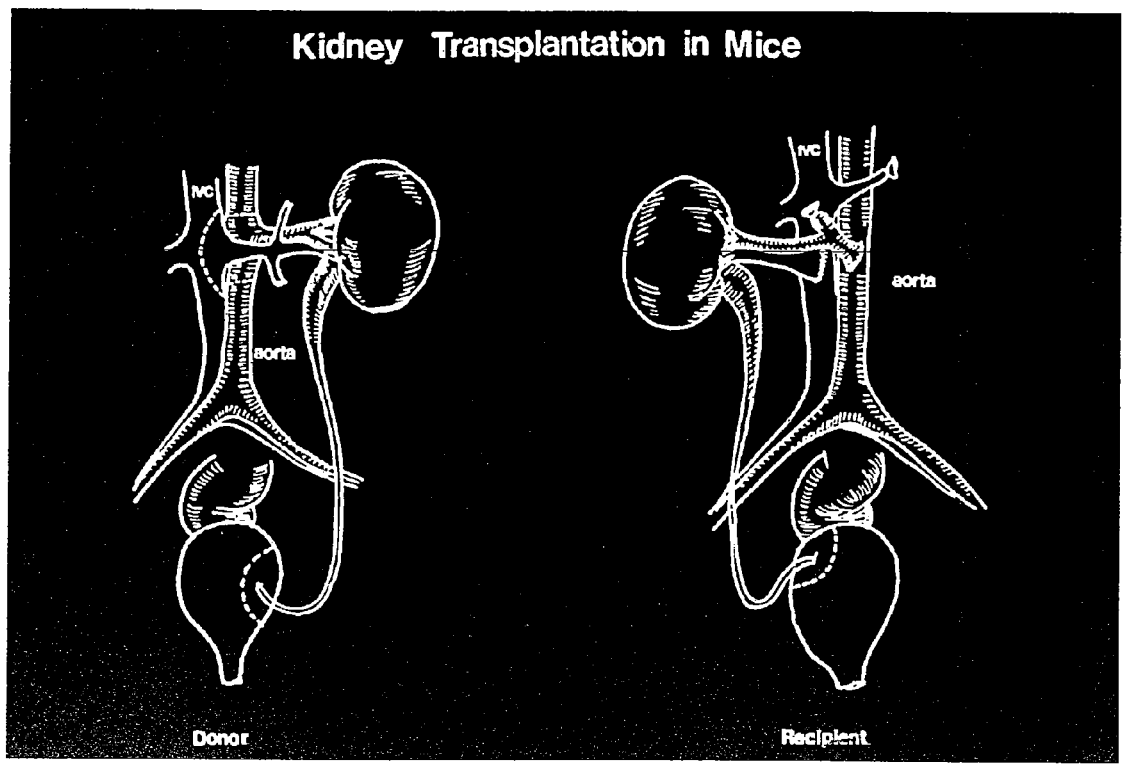
FIG. 1 depicts a surgical model of kidney transplantation in mice.

In accordance with the present invention, it has been surprisingly discovered that the protein Serp-1, a serine protease inhibitor produced by malignant rabbit fibroma virus (MRV) and myxoma virus (MYX), its analogs and biologically active fragments thereof in combination with an anti-rejection agent treats acute and chronic transplant rejection in mammals. The present invention, therefore, is useful for treating transplant rejection. For purposes of the present invention, the terms "treat", "treating" or "treatment" includes preventing, inhibiting, reducing the occurrence of and/or ameliorating the physiological effects of graft rejection. By "graft rejection" is meant allograft and xenograft transplant rejection.

It has also been surprisingly discovered that co-administration of Serp-1 and an anti-rejection agent for a period of about 1 to about 30 days post-transplant is efficacious to treat graft rejection without further administration of an anti-rejection agent. Preferably, Serp-1 and an anti-rejection agent are co-administered for a period of about 8 to about 15 days post-transplantation. It is further contemplated that the period of co-administration of Serp-1 and an anti-rejection agent is substantially continuous by "substantially continuous" is meant over a sequential period of days. For example, Monday through the following Monday.

The present invention, therefore, provides an improved method of treating transplant rejection. While not wishing to be bound by a particular mechanism, it is believed that the anti-rejection agent of the present invention blocks immune complexes which function to ameliorate the reaction to the foreign tissue. Serp-1 inhibits early regulatory inflammatory components. By "early regulatory inflammatory components" is meant the activities of neutrophils, monocytes, macrophages or natural killer (NK) cells. The synergistic effect of the active components of the present invention drastically improves transplantation outcome in both short and long term, resulting in no need for administration of an anti-rejection agent after about 1 to about 30 days of treatment.

In accordance with the present invention transplant rejection is characterized by an acute or chronic diminuation in the physiological function of a transplanted organ. Such diminuation in function is measured by biological factors specific to the organ transplanted. For example, for kidney transplant rejection assessment, increased glomerular atrophy; intimal thickening, tubular atrophy, interstitial fibrosis, lymphocyte infiltration and cortical scarring independently or taken together are indicators of graft, rejection. Similarly, for heart, transplant rejection assessment, increased cardiac vessel disease post-transplant, and increased graft intimal hyperplasia independently or taken together are indicators of graft rejection.

The term "anti-rejection agent" as used herein means any commercially available immunosuppressive pharmaceutical agent which reduces the tendency of a transplanted organ to be rejected by the transplant recipient. Transplant rejection treatment is assessed in accordance with the present invention by one or more of the following organ-dependent parameters decreased coronary graft intimal hyperplasia compared to control grafted vessels; renal function as measured by serial serum creatinine levels; graft survival prolongation; hyalinization and cortical scarring in renal grafts.

Anti-rejection agents in accordance with the present invention are contemplated to include immunosuppressive agents. Anti-rejection agents contemplated by the present invention specifically include but are not limited to cyclosporin (e.g., Cyclosporin A, Sandimmune®, Neoral®, (Novartis), Rapimmune® (American Home Products) FK501 (Fujisawa), CELLCEPT® (Roche, Syntex), IMUREK®, SPANIDIN® and PROGRAF®). The term "subject" as used herein is taken to mean any mammalian patient to which the compositions of the invention may be administered. Subjects specifically intended for treatment with the compositions and methodologies of the present invention include humans, as well as non-human primates, sheep, horses, cattle, goats, pigs, dogs, cats, rabbits, guinea pigs, poultry, hamsters, rats and mice, as well as the organs, derived or originating from these hosts.

In the aforementioned embodiments of the invention, the Serp-1/anti-rejection agent composition is delivered, for treating transplant rejection, in a manner consistent with conventional methodologies associated with transplantation of mammalian organs such as for example, intravenously, intra-articularly, intraperitoneally, intramuscularly, or subcutaneously. In a preferred embodiment Serp-1 is co-administered with cyclosporin (e.g. Cyclosporin A (CsA) or Neoral®).

The preferred Serp-1/CsA combination of the present invention may be administered to a human patient, preferably as a pharmaceutical composition in a therapeutically effective amount. The pharmaceutical compositions of the present invention contain a therapeutically effective dose of the anti-rejection agent and/or combinations of anti-rejection agents and Serp-1 protein, homologs or analogs thereof or a biologically active fragment of the Serp-1 protein, together with a pharmaceutically acceptable carrier. However, it is contemplated that a therapeutically effective amount of anti-rejection agent or combination thereof can be administered from about 1 to about 30 days prior to administration of a therapeutically effective amount of Serp-1 alone and/or Serp-1 together with the anti-rejection agent, to achieve the desired graft-rejection treatment. By "prior" is meant within about one day of the co-administration of the Serp-1/anti-rejection agent combination of the present invention.

The term "therapeutically effective amount" means the dose needed to effectively treat the physiological effects of graft rejection.

As used herein, "analogs" is meant to include substitutions or alterations in the amino acid sequence of the Serp-1 protein, which substitutions or alterations (e.g., additions and deletions) maintain the anti-inflammatory properties of the protein when delivered to the site of inflammation either directed at the site, i.e., locally, or systemically. For purposes of the present invention, the term "analog" includes amino acid insertional derivatives of Serp-1 such as amino and/or carboxyl terminal fusions as well as intrasequence insertions of single or multiple amino acids. Insertional amino acid sequence variants are those in which one or more amino acid residues are introduced into a predetermined site in the protein. Random insertion is also possible with suitable screening of the resulting product. Deletional variants are characterized by removal of one or more amino acids from the sequence. Substitutional amino acid variants are those in which at least one residue inserted in its place. Where the protein is derivatized by amino acid substitution, amino acids are generally replaced by other amino acids having similar physical chemical properties such as hydrophobicity, hydrophilicity, electronegativity, bulky side chains and the like. Examples of conservative substitutions include the substitution of a non-polar (hydrophobic) residue such as isoleucine, valine, leucine or methionine for another. Likewise, the present invention contemplates the substitution of a polar (hydrophilic) residue such as between arginine and lysine, between glutamine and asparagine, and between glycine and serine. Additionally, the substitution of a basic residue such as lysine, arginine or histidine for another or the substitution of an acidic residue such as aspartic acid or glutamic acid, for another is also contemplated.

As used herein, the term "analogs" also encompasses homologs of Serp-1, i.e., corresponding amino acid sequences derived from other serpins and having the same or substantially the same anti-inflammatory properties. As used herein, the term "biologically active fragments" refers to fragments of Serp-1 or Serp-1 analogs which do not encompass the entire length of the Serp-1 polypeptide but which nevertheless maintain the anti-inflammatory properties of the entire Serp-1 polypeptide or analogs thereof when delivered to the site of inflammation either at the site (i.e., locally) or systemically.

Serp-1 amino acid variants may be readily made using peptide synthetic techniques well known in the art such as solid phase peptide synthesis (Merrifield synthesis) and the like or by recombinant DNA techniques well known in the art. Techniques for making substitution mutations at predetermined sites in DNA include, for example, M13 mutagenesis. Manipulation of DNA sequences to produce substitutional, insertional, or deletional variants are conveniently described elsewhere such as Sambrook, et al., 1989, *Molecular Cloning: A Laboratory Manual*, Cold Spring Harbor Laboratories, Cold Spring Harbor, N.Y.

For purposes of the present invention, analogs of Serp-1 also include single or multiple substitutions, deletions and/or additions of any component(s) naturally or artificially associated with the Serp-1 such as carbohydrate, lipid and/or other proteinaceous moieties. All such molecules are encompassed by the term Serp-1 analogs.

In one embodiment of the invention, in order to increase the specific activity of the prepared Serp-1 protein, the cysteine residue at position 244 may be substituted with another amino acid residue, for example alanine. Such a substitution causes the Serp-1 protein to be more biologically active since $Cys^{244}$ is the predicted position for Serp-1 dimer formation through disulfide bridging. Because $Cys^{244}$ lies very close to the reactive center of the Serp-1 protein, Serp-1 dimers are thought to have a disturbed and obfuscated reactive center thereby rendering them biologically inactive. Lomas, et al., 1993, *J. Biol. Chem.,* 268(1):516-521. A mutation at position 244 prevents the formation of Serp-1 dimers in the production of Serp-1 through recombinant DNA means. A decrease in the presence of Serp-1 dimers in a preparative sample is useful since the specific activity of the isolated protein will be increased and thus less protein will be needed in a pharmaceutical preparation.

The inhibitory activity of serpins on serine proteinases is believed to revolve around the slow dissociation of the serpin between the P1 and P1' residues in the active region. Upton, et al. 1990 Virology, 179:618-631. The amino acid sequence Arg/Asp has recently been located at the predicted Serp-1 P1-P1' site (amino acid residues 319 and 320) and is the predicted site for cleavage by serine proteases. Substitutions of either or both of these two amino acids produces Serp-1 analogs of varying biological activities useful in the practice of the present invention. Serp-1 (e.g., mature, processed Serp-1, e.g., having an amino acid sequence obtained from the amino acid sequence of SEQ ID NO: 1) and analogs, homologs and variants of Serp-1 are described in U.S. Pat. No. 5,686,409 entitled "Antirestenosis Protein", and U.S. Pat. No. 5,939,525 entitled "Methods of Treating Inflammation and Compositions Therefor" which teachings are incorporated herein by reference.

The formulation of pharmaceutical compositions is generally known in the art and reference can conveniently be made to Remington's Pharmaceutical Sciences, $17^{th}$ ed., Mack Publishing Co., Easton, Pa. Formulation of the Serp-1 protein/anti-rejection agent for use in the present invention must be stable under the conditions of manufacture and storage and must also be preserved against the contaminating action of microorganisms such as bacteria and fungi. Prevention against microorganism contamination can be achieved through the addition of various antibacterial and antifungal agents.

The pharmaceutical forms of Serp-1/anti-rejection agent suitable for infusion include sterile aqueous solutions or dispersions and sterile powders for the extemporaneous preparation of sterile injectable solutions or dispersion. In all cases, the form must be sterile and must be fluid to the extent that easy syringability exists. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants, or vegetable oils. Sterilization can be accomplished by any art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject composition is accomplished by incorporating these compounds in the required amount in the appropriate solvent with various ingredients enumerated above, as required, followed by sterilization, preferably filter sterilization. To obtain a sterile powder, the above solutions are vacuum dried or freeze-dried as necessary.

The subject compositions are thus compounded for convenient and effective administration in pharmaceutically effective amounts with a suitable pharmaceutically acceptable carrier in a therapeutically effective dose.

As used herein, the term "pharmaceutically acceptable carrier and/or diluent" includes any and all solvents, dispersion media, antibacterial and antifungal agents, microcapsules, liposomes, cationic lipid carriers, isotonic and absorption delaying agents and the like which are not incompatible with the active ingredients e.g., Serp-1, cyclosporin A, Rapimmune® or FK501. The use of such media and agents for pharmaceutically active substances is well known in the art. Supplementary active ingredients may also be incorporated into the compositions and used in the methods of the present invention. Supplementary active ingredients contemplated by the present invention, include, but are not limited to, corticosteroids.

The precise therapeutically-effective amount of e.g. Serp-1/cyclosporin A to be used in the methods of this invention applied to humans can be determined by the ordinarily skilled artisan with consideration of individual differences in age, weight, organ size and condition of the patient. It can generally be stated that the Serp-1/anti-rejection agent pharmaceutical preparation of the present invention should be preferably administered in an amount of at least about 1 pg/kg to about 1 g/kg per infusion dose, more preferably in an amount up to about 3 μg/kg to about 1 mg/kg per dose.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly depend on the unique characteristics of the active material (e.g., Serp-1 protein, cyclosporin A, Neoral®, FK501, Rapimmune®) and the limitations inherent in the art of compounding such an active material for the treatment of transplant rejection as herein disclosed in detail.

The principal active ingredients are compounded for convenient and effective administration in effective amounts with a suitable pharmaceutically acceptable carrier in dosage unit form as hereinabove disclosed. A unit dosage form can, for example, contain the principal active compound in amounts ranging from about 1 pg/kg to about 1 g/kg. The anti-rejection agent (e.g. Cyclosporin A) or combinations of antirejection agents (e.g., Cyclosporin A and FK501) are contained in a unit dosage form in amounts ranging from about 1 mg/kg to about 20 mg/kg. Where combinations of anti-rejection agents are employed, it is contemplated that the total unit dosage form of such agents ranges from about 1 mg/kg to about 40 mg/kg. In the case of compositions containing supplementary active ingredients, the dosages are determined by reference to the usual dose and manner of administration of the ingredients.

Packaging material used to contain the e.g. Serp-1/CsA active ingredients can comprise glass, plastic, metal or any other suitable inert material so long as the packaging material does not chemically react with any of the ingredients contained therein.

The composition of the present, invention may be administered in a manner compatible with the dosage, formulation and in such amount as will be therapeutically effective. The compositions of the invention may be administered in any way which is medically acceptable which may depend on the type of transplant to be treated. Possible administration routes include injections, by parenteral routes such as intravascular, intravenous, intra-arterial, subcutaneous, intramuscular, intraperitoneal, intraventricular, intraepidural, or others. The compositions may also be directly (topically) applied to tissue surfaces during transplantation. Sustained release administration is also specifically included in the invention, by such means as depot injections or erodible implants.

The invention is further illustrated by the following specific examples which are not intended in any way to limit the scope of the invention.

EXAMPLE 1

Serp-1/CsA Prevented Chronic Allograft Rejection in a Rat Kidney Model

F344 male rats served as donors and Lewis rats as recipients for orthotopic kidney transplant. Recipients' native kidneys were removed at the time of surgery (FIG. 1). Animal survival depended entirely on the function of the transplanted kidney. Animals received subtherapeutic CsA (0.75 mg/kg sc) for 0.10 days to prevent initial acute rejection. Greater than 60% of animals were expected to survive to post-operative day (POD) 140 and exhibit features of chronic renal allograft rejection (i.e. intimal thickening, glomerular sclerosis, tubular atrophy, interstitial as well as cortical fibrosis). These animals were included in our final analysis.

Groups
  Group 1: F344 to Lewis with CsA, n=10 (Control);
  Group 2: F344 to Lewis with CsA+Serp-1 10 ng/g. IV Post-Operative Day (POD) 0-10-intermediate dose, n=12;
  Group 3: F344 to Lewis with CsA+Serp-1 50 ng/g IV POD 0-100 high dose, n=12;
Assessment
  1) Serial serum creatinine levels on POD 0.140.
  2) CsA levels on POD 7.
  3) Routine pathology on POD-140.
Results
Survival and Function Table 1 shows the survival, CsA levels and renal function. 91% and 67% of the animals survived until sacrifice at 140 days (P>0.05 vs controls). All animals treated with Serp-1 had 100-120 g weight gains and no side effects were found in these animals. Renal function, as measured by serum creatinine levels in the Serp-1 high dose treated group, were significantly better than those in the controls (P<0.01).

Histopathological Findings at Necropsy

Microscopic Hematoxylin-Eosin (HE) and tricrone staining slides were blindly-read by Dr. B. Garcia, Professor of Pathology, The University of Western Ontario. The severity of chronic rejection was scored as: 0—no changes, 1—minimal changes, 2—mild changes, 3—moderate changes and 4—marked changes. The median score of histopathological changes and percentage of positive cases are presented in Table 2.

Figure 2:
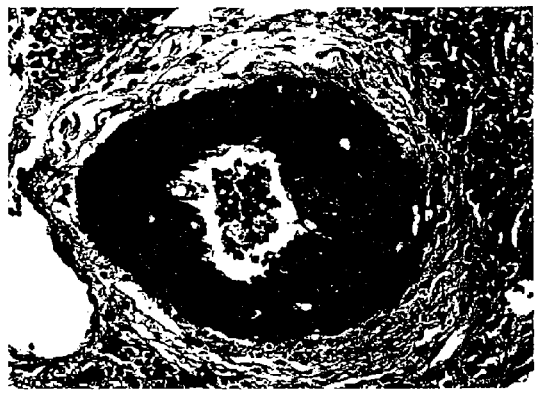
FIG. 2 shows a histopathological comparison of Serp-1 treated renal allografts with controls.
Figure 2:
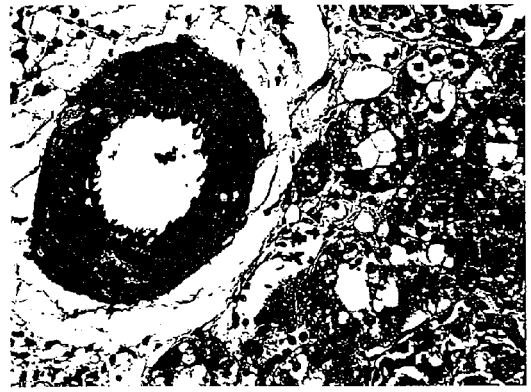
Figure 2:
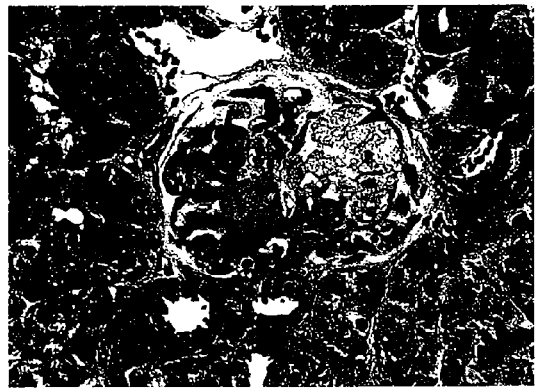
Figure 2:

Renal allografts in the control group developed typical chronic rejection characterized by intimal thickening, hyalinization and cortical scarring (FIG. 2A). In contrast, there were only minimal or no vascular changes in the renal allografts treated with the combination of low dose of CsA and a short course of high dose Serp-1 (FIG. 2B). There was no histological improvement in the renal allografts treated with an intermediate dose of Serp-1.

The results demonstrated that a short course of Serp-1/CsA significantly improved renal function and histology, thus preventing chronic transplant rejection in this model. This data suggest that viral protein (Serp-1) combined with a low dose of CsA can be used in clinical transplantation to prevent graft rejection.

TABLE 1

Survival and Creatinine Levels

| Group | Survival (days) | Creatinine (mg/L) |
|---|---|---|
| Allograft + CsA 0.75 mg/kg (control) | >140 × 7 >>28, 30, 32, 43 | 103 ± 42 |
| Allograft + CsA 0.75 mg/kg + Serp-1 10 ng/g | >140 × 10 >>121 | 58 ± 25 |
| Allograft + CsA 0.75 mg/kg + Serp-1 50 ng/g | >140 × 8 >>6, 7, 120, 135 | 45 ± 6** |

Note:
CsA given SC on POD 0-9
Serp-1 given IV on POD 0-10
>>sacrificed
**p = 0.029 vs. experimental control

TABLE 2

Histopathological changes

| | Allograft | Allograft + viral protein/CsA (med. dose) n = 10 | Allograft + viral protein/CsA (high dose) n = 8 |
|---|---|---|---|
| Glomerular | | | |
| Loss | 33% (0.0) | 30% (0.0) | 13% (0.0) |
| Vascular | | | |
| Endothelitis | 28% (1.0) | 10% (0.0) | 0 |
| Intimal thickening | 100% (3.0) | 70% (2.0) | 25% (0.0) * |
| Cortical scarring | 71% (1.0) | 70% (1.0) | 13% (0.0) * |

Note:
data are percentage of animals showing evidence of indicated injury pattern;
number in parentheses indicates median injury score;
Control = CsA 0.75 mg/kg subcutaneously (SC) on Post-Operative Day (POD) 0-9;
experimental control = CsA 0.75 mg/kg SC on POD 0-9 + saline 2 cc IV on POD 0-10;
viral protein med. dose = CsA 0.75 mg/kg SC on POD 0-9 + Serp-1 10 ng/g IV on POD 0-10;
viral protein high dose = CsA 0.75 mg/kg SC on POD 0-9 + Serp-1 50 ng/g IV on POD 0-10;
* P < 0.05, vs control, Mann-Whitney test

EXAMPLE 2

Figure 3:
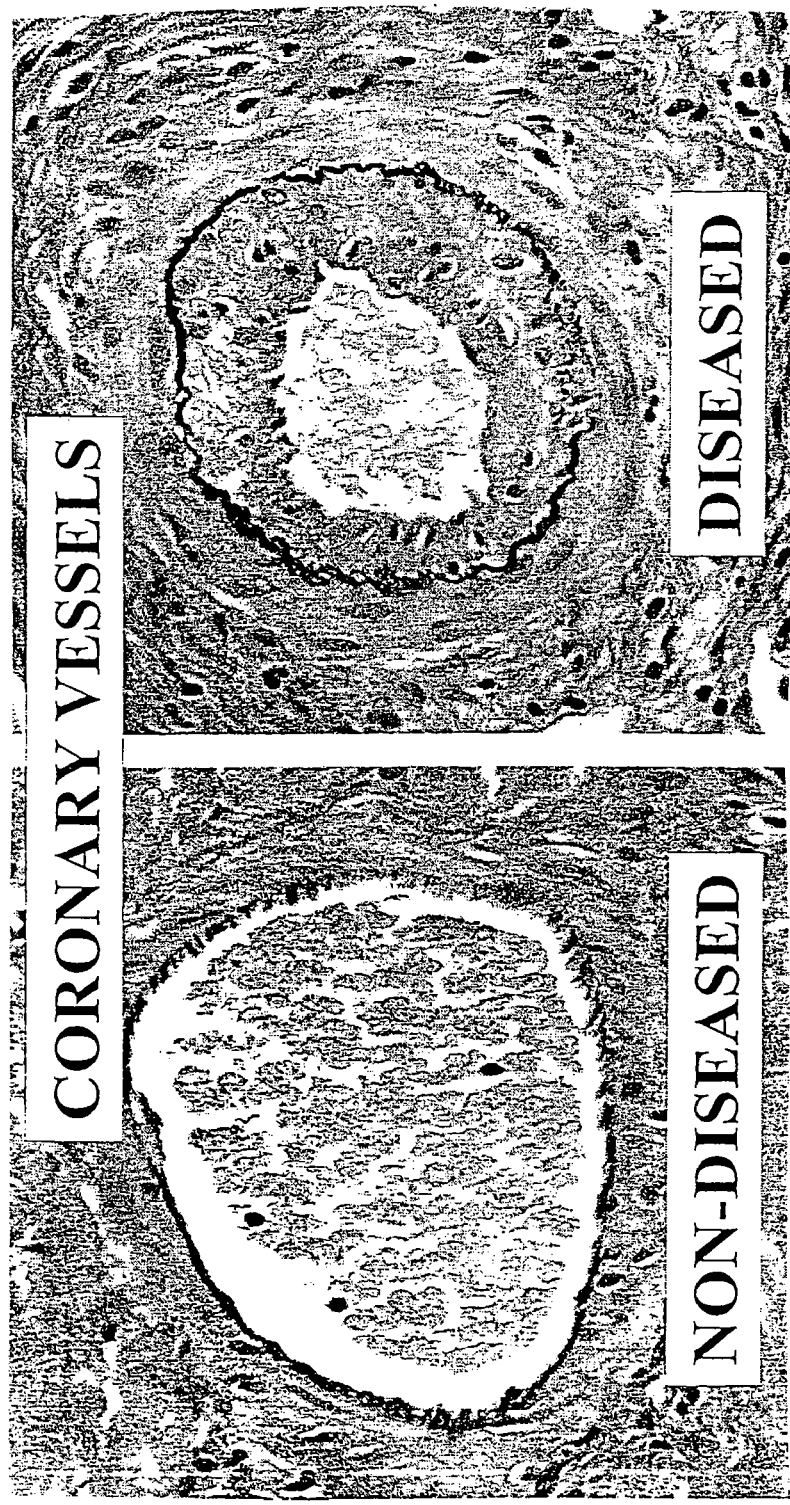
FIG. 3 shows that Serp-1/Neoral® produces significant decreases in the percentage of diseased coronary vessels versus controls.

Treatment of recipient rats in a model of heterotopic heart transplantation with Serp-1 and Neoral® Cyclosporin (CsA) prevented the development of graft vascular disease (FIG. 3).

The most commonly used model for preclinical research on graft vascular disease is a model in which a heterotopic heart transplantation is performed in MHC mismatched rats. In this model, rodents treated with cyclosporin A for only the first 7 days after transplantation, developed graft vascular disease when analyzed after sacrifice at postoperative day 90.

Based on our most recent experience with this model, we used the PVG to ACI strain combination in which the recipient was treated with 7.5 mg/kg Neoral® per gavage from day 0 to day 9. In this model the incidence of acute rejection (and therefore loss of the animal) was 30%. The average luminal narrowing in this model was 50% at day 90.

Figure 4:
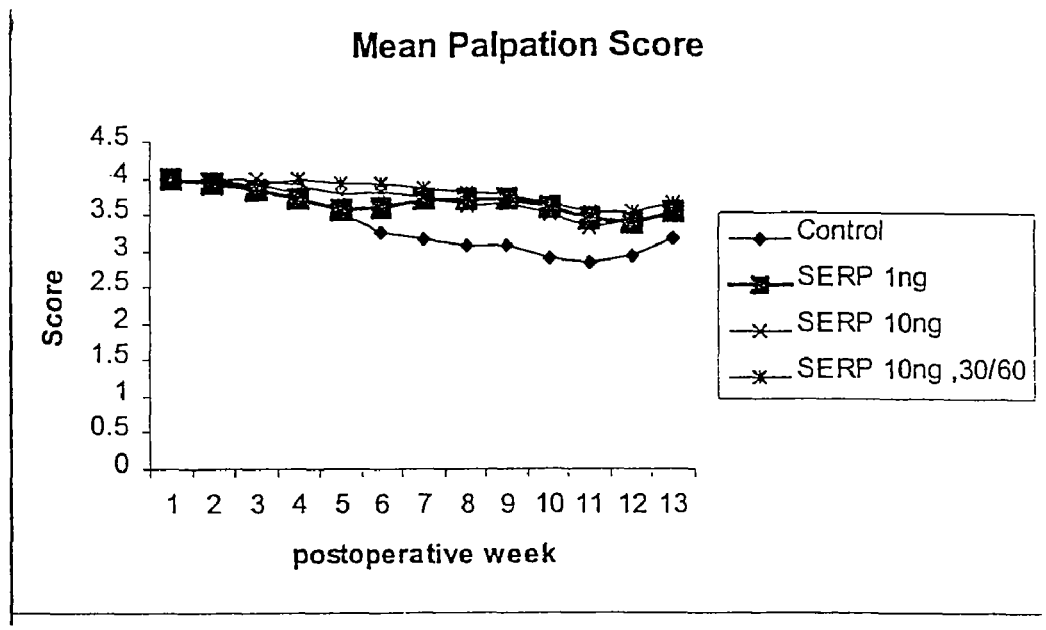
FIG. 4 depicts the mean palpation score of the four groups over a 13 week follow-up period. The mean palpation score of the control group was lower than in the three groups treated with Serp-1 and Neoral®.
Figure 5:
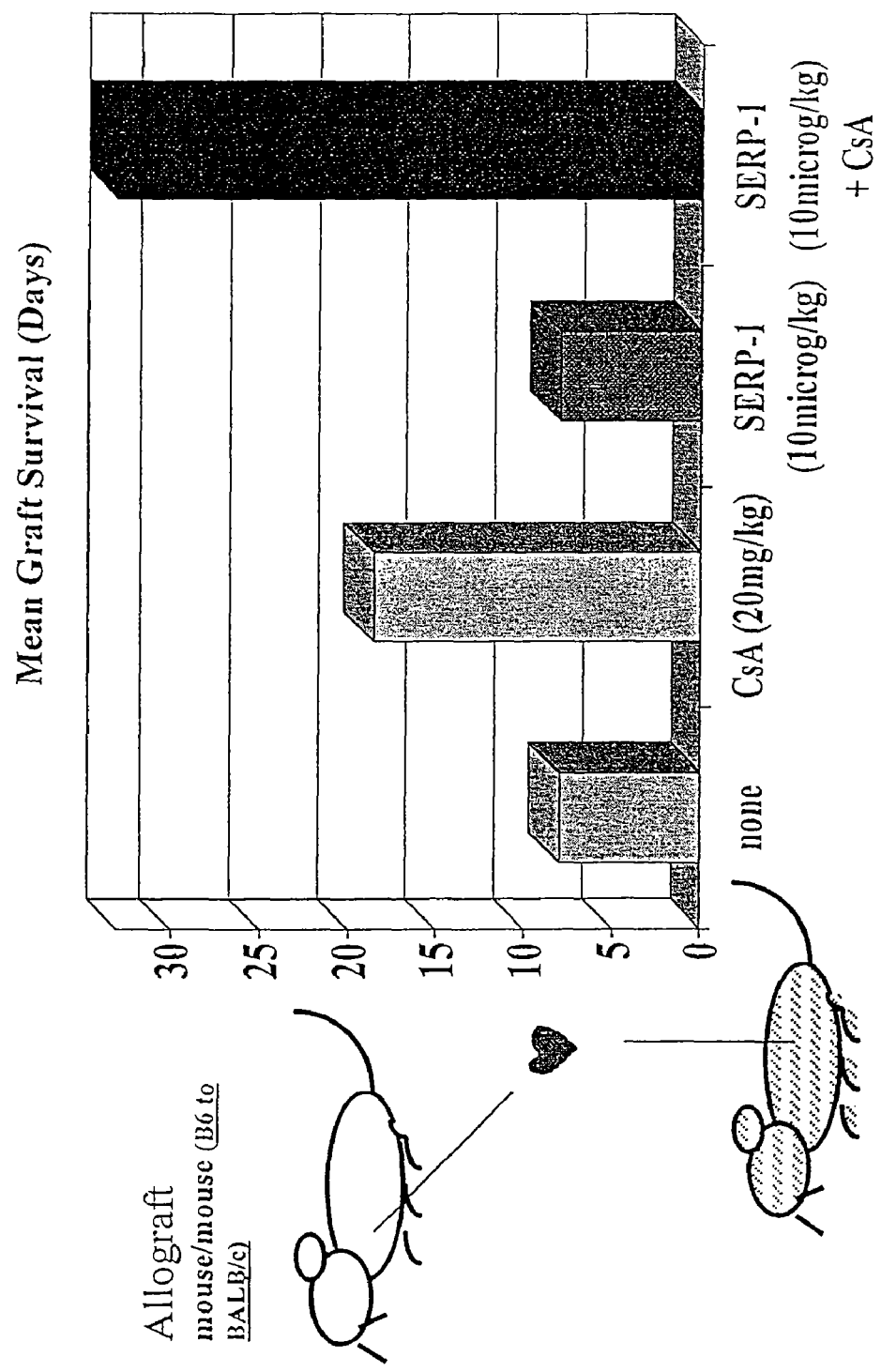
FIG. 5 shows that Serp-1/CsA protects coronary vessels from graft vascular disease versus CsA treatment alone.

For the model of heterotopic heart transplantation in rats the pulmonary veins and the venae cava were tied off at the time of graft harvest in the donor animal. The heart was perfused with a preservation solution and then immediately implanted into the recipient animal. This was accomplished by anastomizing the donor aorta to the recipient abdominal aorta and the donor pulmonary artery to the recipient vena cava. The vascular clamps were then removed and following reperfusion of the donor organ the heart started beating. Thus, a primary vascularized, non-working heart transplantation model was created. Graft function was monitored by daily palpation. The quality of graft function was scored on a scale of 0 to 4, where 0 was a non-beating allograft and 4 was considered a vigorously beating heart allograft. Acute rejection was diagnosed clinically if the palpation score was less than 1. Subacute rejection in this model was defined if the palpation score was less than or equal to 2 with histologic evidence of massive inflammatory infiltrates. The recipient animals were followed for 90 days at which time the animal, was sacrificed. The heart was excised. Thin hematoxylin and eosin (H&E) stained sections of paraffin embedded samples were assessed by a pathologist blinded to the treatment regimen for the presence of graft vascular disease. The pathologist scored the individual vessel based on a five-point grading scale (0=no involvement, 1=partial intimal involvement, 2=concentric intimal thickening, 3=severe concentric involvement with up to 50% luminal narrowing, 0.4=more than 50% luminal narrowing). In addition the lesions were quantified by morphometric analysis. The score and mean morphometrically assessed narrowing were then compared between the individual experimental groups (FIG. 4).

Experimental Groups
  Group 1 (control): Neoral® monotherapy (7.5 mg/kg Post-Operative Day (poday) 0-9).
  Group 2 (Serp-1 ng/g): Neoral® (7.5 mg/kg poday 0-9) plus Serp-1 at 1 ng/g IV poday 0-9.
  Group 3 (Serp-10 ng/g). Neoral® (7.5 mg/kg poday 0-9) plus Serp-1 at 10 ng/g IV poday 0-9.
  Group 4 (Serp-10 ng/g+30+60): Neoral® 7.5 mg/kg poday 0-9) plus Serp-1 at 10 ng/g IV poday 0-9; Readministration of Serp-1 (10 ng/g)+. Neoral® (7.5 mg/kg) at post-operative day 30 and 60.

Follow-Up Period
  90 days, then sacrifice.

Follow-Up Parameters:
  Assessment of graft palpation score: 4=strong beating, 3=moderately beating, 2=weakly beating, 1=not beating.
  Assessment of weight during days of drug treatment and at the time of sacrifice. Weight was expressed as percentage weight change in comparison to the weight at the time of surgery.

Morphometric Analysis
  Each heart was cut horizontally along the long-axis of the graft and 4 sections were stained with H & E.

All coronary arteries were identified in each section and analyzed separately by morphometry.

Morphometric analysis included determination of the free, unoccluded vessel lumen, the vessel area inside the basal membrane (intima plus free lumen) and the total vessel area.

Morphometric outcome variables were:
  (a) number of vessels diseased, where disease was defined as any noticeable amount of intima; and
  (b) percent intimal area; vessel area inside the basal membrane minus the free lumen divided by the vessel area inside the basal membrane.

Results

Graft Survival
  Group 1: 1 animal (#2) rejected the graft at post-operative day 14, another rejected at post-operative day (POD) 7 (#10).
  Group 2: 1 animal (#10) rejected the graft at post-operative day 31.
  Group 3: all allografts were beating by the end of the follow-up period.
  Group 4: all allografts were beating by the end of the follow-up period.

Graft Palpation Score:
  The graft palpation score is depicted as the median of each week of follow-up for each animal of each individual group.

Group 1 (Control)

| | WEEK | | | | | | | | | | | | |
|---|---|---|---|---|---|---|---|---|---|---|---|---|---|
| Animal | 1 | 2 | 3 | 4 | 5 | 6 | 7 | 8 | 9 | 10 | 11 | 12 | 13 |
| 1 | 4 | 4 | 4 | 4 | 4 | 4 | 4 | 4 | 4 | 4 | 4 | 4 | 4 |
| 2 | 4 | 4 | — | — | — | — | — | — | — | — | — | — | — |
| 3 | 4 | 4 | 4 | 4 | 4 | 4 | 4 | 4 | 4 | 4 | 4 | 4 | 4 |
| 4 | 4 | 4 | 4 | 4 | 4 | 4 | 4 | 4 | 4 | 4 | 4 | 4 | 4 |
| 5 | 4 | 4 | 4 | 3 | 3 | 3 | 3 | 3 | 3 | 3 | 2 | 2 | 2 |
| 6 | 4 | 4 | 4 | 4 | 4 | 3 | 3 | 3 | 3 | 2 | 2 | 2 | 3 |
| 7 | 4 | 4 | 4 | 4 | 4 | 3 | 3 | 3 | 3 | 2 | 2 | 2 | 3 |
| 8 | 4 | 4 | 4 | 4 | 4 | 4 | 4 | 4 | 4 | 4 | 4 | 4 | 4 |
| 9 | 4 | 4 | 4 | 4 | 3 | 2 | 2 | 2 | 2 | 1 | 1 | 1 | 2 |
| 10 | 4 | — | — | — | — | — | — | — | — | — | — | — | — |
| 11 | 4 | 4 | 4 | 4 | 3 | 3 | 3 | 3 | 3 | 1 | 1 | 1 | 2 |
| 12 | 4 | 3 | 3 | 3 | 4 | 3 | 3 | 3 | 4 | 4 | 4 | 4 | 4 |
| 13 | 4 | 4 | 4 | 3 | 2 | 2 | 2 | 2 | 2 | 2 | 2 | 3 | 3 |
| 14 | 4 | 4 | 4 | 4 | 4 | 4 | 3 | 3 | 3 | 3 | 3 | 3 | 3 |
| 15 | 4 | 4 | 4 | 4 | 3 | 3 | 2 | 2 | 2 | 2 | 3 | 3 | 3 |

Group 2—Serp-1 (1 ng/g)+Neoral® (7.5 mg/g)

| | WEEK | | | | | | | | | | | | |
|---|---|---|---|---|---|---|---|---|---|---|---|---|---|
| Animal | 1 | 2 | 3 | 4 | 5 | 6 | 7 | 8 | 9 | 10 | 11 | 12 | 13 |
| 1 | 4 | 4 | 4 | 3 | 3 | 3 | 3 | 3 | 3 | 3 | 3 | 3 | 3 |
| 2 | 4 | 4 | 4 | 4 | 4 | 4 | 4 | 3 | 3 | 3 | 3 | 3 | 3 |
| 3 | 4 | 4 | 4 | 4 | 4 | 4 | 4 | 4 | 4 | 4 | 4 | 4 | 4 |
| 4 | 4 | 4 | 4 | 4 | 4 | 4 | 4 | 3 | 3 | 3 | 1 | 1 | 2 |
| 5 | 4 | 4 | 4 | 4 | 4 | 4 | 4 | 4 | 4 | 4 | 4 | 4 | 4 |
| 6 | 4 | 4 | 3 | 3 | 3 | 4 | 4 | 4 | 4 | 4 | 4 | 4 | 4 |
| 7 | 4 | 4 | 4 | 4 | 4 | 4 | 4 | 4 | 4 | 4 | 4 | 4 | 4 |
| 8 | 4 | 4 | 4 | 4 | 4 | 4 | 4 | 4 | 4 | 4 | 4 | 4 | 4 |
| 9 | 4 | 4 | 4 | 4 | 4 | 4 | 4 | 4 | 4 | 4 | 4 | 4 | 4 |
| 10 | 4 | 3 | 3 | 1.5 | 0 | 0 | 0 | — | — | — | — | — | — |
| 11 | 4 | 4 | 4 | 4 | 4 | 4 | 4 | 4 | 4 | 4 | 4 | 4 | 4 |
| 12 | 4 | 4 | 4 | 4 | 4 | 3 | 3 | 3 | 3 | 2 | 2 | 2 | 2 |
| 13 | 4 | 4 | 4 | 4 | 4 | 4 | 4 | 4 | 4 | 4 | 4 | 4 | 4 |
| 14 | 4 | 4 | 4 | 4 | 4 | 4 | 4 | 4 | 4 | 3 | 3 | 3 | 3 |
| 15 | 4 | 4 | 4 | 4 | 4 | 4 | 4 | 4 | 4 | 4 | 4 | 3.5 | 4 |

Group 3—Serp-1 (10 ng/g)+Neoral® (7.5 mg/kg)

| Animal | \multicolumn{13}{c}{WEEK} |
|---|---|---|---|---|---|---|---|---|---|---|---|---|---|
| | 1 | 2 | 3 | 4 | 5 | 6 | 7 | 8 | 9 | 10 | 11 | 12 | 13 |
| 1 | 4 | 4 | 4 | 4 | 4 | 4 | 4 | 4 | 4 | 4 | 4 | 4 | 4 |
| 2 | 4 | 4 | 4 | 4 | 4 | 4 | 4 | 4 | 4 | 4 | 4 | 4 | 4 |
| 3 | 4 | 4 | 4 | 4 | 4 | 4 | 4 | 4 | 4 | 4 | 3 | 3 | 3 |
| 4 | 4 | 4 | 4 | 4 | 4 | 4 | 4 | 4 | 4 | 4 | 4 | 4 | 4 |
| 5 | 4 | 4 | 4 | 4 | 4 | 4 | 4 | 4 | 4 | 3 | 3 | 3 | 4 |
| 6 | 4 | 4 | 4 | 4 | 4 | 4 | 4 | 4 | 4 | 3 | 3 | 3 | 3 |
| 7 | 4 | 4 | 4 | 4 | 4 | 4 | 4 | 4 | 3 | 3 | 3 | 3 | 4 |
| 8 | 4 | 4 | 4 | 4 | 4 | 4 | 4 | 4 | 4 | 4 | 4 | 4 | 4 |
| 9 | 4 | 4 | 4 | 4 | 4 | 4 | 4 | 4 | 4 | 3 | 3 | 3.5 | |
| 10 | 4 | 4 | 4 | 4 | 3 | 3 | 3 | 3 | 3 | 3 | 3 | 3 | 3 |
| 11 | 4 | 4 | 4 | 4 | 4 | 4 | 4 | 4 | 4 | 4 | 4 | 4 | 4 |
| 12 | 4 | 4 | 4 | 4 | 3 | 3 | 2 | 2 | 2 | 2 | 2 | 2 | 2 |
| 13 | 4 | 4 | 4 | 3 | 3 | 3 | 2 | 2 | 2 | 2 | 2 | 2 | 2 |
| 14 | 4 | 4 | 4 | 4 | 4 | 4 | 4 | 4 | 4 | 4 | 4 | 4 | 4 |
| 15 | 4 | 4 | 4 | 4 | 4 | 4 | 4 | 4 | 4 | 4 | 4 | 4 | 4 |

Group 4—Serp-1 (10 ng/g)+Neoral® (7.5 mg/kg); Readministration at Day 30 and Day 60 Post-Operation

| Animal | \multicolumn{13}{c}{WEEK} |
|---|---|---|---|---|---|---|---|---|---|---|---|---|---|
| | 1 | 2 | 3 | 4 | 5 | 6 | 7 | 8 | 9 | 10 | 11 | 12 | 13 |
| 1 | 4 | 4 | 4 | 4 | 4 | 4 | 4 | 4 | 4 | 4 | 4 | 4 | 4 |
| 2 | 4 | 4 | 3 | 4 | 4 | 4 | 4 | 4 | 4 | 4 | 4 | 3 | 4 |
| 3 | 4 | 4 | 3 | 4 | 4 | 4 | 4 | 4 | 4 | 4 | 4 | 4 | 4 |
| 4 | 4 | 4 | 4 | 4 | 4 | 4 | 4 | 4 | 4 | 4 | 4 | 4 | 4 |
| 5 | 4 | 4 | 4 | 4 | 4 | 4 | 4 | 4 | 4 | 4 | 4 | 4 | |
| 6 | 4 | 4 | 4 | 4 | 4 | 4 | 4 | 4 | 4 | 4 | 3 | 3 | 3 |
| 7 | 4 | 4 | 4 | 4 | 4 | 4 | 4 | 4 | 4 | 4 | 4 | 4 | 4 |
| 8 | 4 | 4 | 4 | 4 | 4 | 4 | 3 | 3 | 3 | 2 | 1 | 2 | 1.5 |
| 9 | 4 | 4 | 4 | 4 | 4 | 4 | 4 | 4 | 3 | 3 | 3 | 3.5 | |
| 10 | 4 | 4 | 4 | 4 | 4 | 4 | 4 | 4 | 4 | 4 | 4 | 4 | |
| 11 | 4 | 4 | 4 | 4 | 4 | 4 | 3.5 | 3 | 3 | 3 | 3 | 3 | 3 |
| 12 | 4 | 4 | 4 | 4 | 4 | 4 | 4 | 4 | 4 | 4 | 4 | 4 | 4 |
| 13 | 4 | 4 | 4 | 4 | 3 | 3 | 3 | 3 | 3 | 3 | 3 | 3 | 3 |
| 14 | 4 | 4 | 4 | 4 | 4 | 4 | 4 | 4 | 4 | 4 | 4 | 4 | 4 |
| 15 | 4 | 4 | 4 | 4 | 4 | 4 | 4 | 4 | 4 | 4 | 4 | 4 | 4 |

Morphometric Analysis

A total of 1658 coronary arteries from 58 allografts were analyzed by morphometry. The number of vessels and the number of diseased coronary arteries per allograft are depicted in the following tables.

Number of Coronaries Per Allograft

| ANIMAL | Control | 1 ng/kg Serp-1 | 10 ng/kg Serp-1 | 10 ng/kg Serp-1 + d30 + d60 |
|---|---|---|---|---|
| 1 | 30 | 24 | 26 | 31 |
| 2 | | 27 | 34 | 38 |
| 3 | 32 | 22 | 26 | 32 |
| 4 | 28 | 26 | 12 | 43 |
| 5 | 18 | 24 | 34 | 33 |
| 6 | 26 | 24 | 39 | 31 |
| 7 | 29 | 31 | 39 | 47 |
| 8 | 24 | 21 | 23 | 35 |
| 9 | 20 | 26 | 34 | 42 |
| 10 | | 5 | 34 | 37 |
| 11 | 22 | 29 | 24 | 27 |
| 12 | 37 | 26 | 32 | 43 |
| 13 | 32 | 19 | 15 | 23 |
| 14 | 20 | 23 | 37 | 41 |
| 15 | 22 | 10 | 40 | 29 |

Number of Diseased Coronaries Per Allograft

| ANIMAL | Control | 1 ng/kg Serp-1 | 10 ng/kg Serp-1 | 10 ng/kg Serp-1 + d30 + d60 |
|---|---|---|---|---|
| 1 | 3 | 10 | 6 | 2 |
| 2 | | 5 | 3 | 4 |
| 3 | 8 | 0 | 4 | 6 |
| 4 | 3 | 3 | 0 | 4 |
| 5 | 4 | 1 | 4 | 3 |
| 6 | 4 | 0 | 4 | 8 |
| 7 | 14 | 5 | 10 | 4 |
| 8 | 1 | 3 | 2 | 1 |
| 9 | 4 | 8 | 2 | 7 |
| 10 | | 5 | 6 | 3 |
| 11 | 13 | 4 | 6 | 4 |
| 12 | 6 | 10 | 0 | 4 |
| 13 | 3 | 4 | 5 | 3 |
| 14 | 7 | 2 | 2 | 5 |
| 15 | 11 | 2 | 4 | 5 |

Percentage of Diseased Vessels Per Allograft
Percentage of Diseased Coronaries Per Allograft

| ANIMAL | Control | 1 ng/kg Serp-1 | 10 ng/kg Serp-1 | 10 ng/kg Serp-1 + d30 + d60 |
|---|---|---|---|---|
| 1 | 10.0% | 41.7% | 23.1% | 6.5% |
| 2 | | 18.5% | 8.8% | 10.5% |
| 3 | 25.0% | 0.0% | 15.4% | 18.8% |
| 4 | 10.7% | 11.5% | 0.0% | 9.3% |
| 5 | 22.2% | 4.2% | 11.8% | 9.1% |
| 6 | 15.4% | 0.0% | 10.3% | 25.8% |
| 7 | 48.3% | 16.1% | 25.6% | 8.5% |
| 8 | 4.2% | 14.3% | 8.7% | 2.9% |
| 9 | 20.0% | 30.8% | 5.9% | 16.7% |
| 10 | | 100.0% | 17.6% | 8.1% |
| 11 | 59.1% | 13.8% | 25.0% | 14.8% |
| 12 | 16.2% | 38.5% | 0.0% | 9.3% |
| 13 | 9.4% | 21.1% | 33.3% | 13.0% |
| 14 | 35.0% | 8.7% | 5.4% | 12.2% |
| 15 | 50.0% | 20.0% | 10.0% | 17.2% |

Percentage of Diseased Vessels Per Group

| GROUP | Total | Non diseased Count | Diseased Count | Percent |
|---|---|---|---|---|
| Control | 340 | 259 | 81 | 23.8% |
| 1 ng/kg Serp-1 | 337 | 275 | 62 | 18.4% |
| 10 ng/kg Serp-1 | 449 | 391 | 58 | 12.9% |
| 10 ng/kg Serp-1 + d30 + 360 | 532 | 469 | 63 | 11.8% |

Coadministration of Serp-1 and Neoral® is able to decrease the number of diseased coronary vessels.

EXAMPLE 3

The efficacy of Serp-1 (1 ng/g-10 µg/g) in combination with Cyclosporin A (at doses of 5 mg/kg/day-20 mg/kg/day) for the treatment of acute and chronic transplant rejection were assessed in a heterotopic mouse heart allograft transplant model (FIG. 6).

Details of Animal Surgical Protocols:

The heterotopic heart transplant model was performed as previously described. *Transplantation* 62:1267). Briefly, a median sternotomy was performed in the donor, and the right and left superior vena cave were ligated. The ascending aorta and pulmonary artery of the donor were anastomosed end to side to the recipient aorta and inferior vena cava, respectively.

Acute Rejection Model:

For the acute rejection model, male inbred mice C57BL/6 ($H2^b$) and BALB/c($H2^d$) were used as the donor and the recipient, respectively. This strain combination was mismatched in both major and minor MHC. We have previously demonstrated that the graft was rejected in 9 days after grafting Zhong, et. al. (supra).

Criteria for Rejection:

Direct palpation of heart grafts was performed daily. Complete cessation of cardiac impulses was considered as the end point of rejection. The animal was sacrificed and necropsy performed. The following criteria were used for assessing rejection: lymphocytic infiltration, vasculitis, infarction, ischemia, and thrombosis. Animals were followed up until development of end point rejection or sacrifice at 30 days for acute rejection.

Results:

1. Serp-1 alone: no prolongation in graft survival using doses from 1 ng/g Post-operative day (POD 0, 2, 4 & 7), 10 ng/g (POD 0) or 1 µg (POD 0-8) (n+4, 1&1).

2. Serp-1 (10 ng/g IV POD 0, 2, 4&7)+CsA (20 mg/kg) vs CsA alone: significant prolongation of graft survival (36 vs 18.5 days, p<0.05) but hearts not beating strongly (n=4).

3. Serp—1+CsA. (5 mg/kg) vs CsA alone: no prolongation of graft survival (n=4).

Heart Allografts—B6 to BALB/c Mice

| Treatment | Dose | Graft Survival (days) | Mean |
|---|---|---|---|
| Serp-1* | 1 ng/g IV POD 0, 2, 4 & 7 | 7, 8, 8, 8 | 7.75 |
|  | 10 ng/g IV POD 0 | 8 | 8 |
| Serp-1 + CsA# | Serp-1 10 ng/g IV POD 0, 2, 4 & 7 CsA 20 mg/kg IM POD 0-7 then every other day until day 28 | 25, 33, 37, >38 | >33.3 |
| CsA+ | CsA 20 mg/kg IM POD 0-7 then every other day until day 28 | 14, 17, 18, 26 | 18.5 |
| None |  |  | 8 |

EXAMPLE 4

The efficacy of Serp-1 (100 ng/g) in combination with Cyclosporin A (at doses of 0.25 mg/kg/day-0.5 mg/kg/day) for the treatment of acute transplant rejection was assessed in a heterotopic rat heart allograft, transplant model.

Details of Animal Surgical Protocols:

The heterotopic heart transplant model was performed as described in Example 3.

Acute Rejection Model:

For the acute rejection models, Brown-Norway and Lewis rats were used as the donor and the recipient respectively.

Criteria for Rejection:

Direct palpation of heart allografts was performed daily. Complete cessation of cardiac impulses was considered as the point of rejection. The following criteria were used for assessing rejection: lymphocytic infiltration, vasculitis, infarction, ischemia, and thrombosis. Animals were followed up until development of end point rejection or sacrifice at 30 days for acute rejection.

Results:

1. Cyclosporin A (CsA) alone: no prolongation in graft survival using doses of 0.25 mg/kg and 0.5 mg/kg, daily (n=8).

2. Serp-1 (100 ng/g IV post operative day 0-10)+CsA (0.5 mg/kg) vs. CsA alone (0.5 mg/kg daily) significant prolongation of graft survival (>73 vs. 33.5 days) (n=8).

3. Serp-1 (100 ng/g IV post-operative day 0-10)+CsA (0.25 mg/kg) vs. CsA alone (0.25 mg/kg, daily): significant prolongation of graft survival (>26.25 vs. 12.88) (n=8).

Heart Allografts—Brown Norway to Lewis Rats

| Treatment | Dose | Graft Survival (Days) | Mean |
|---|---|---|---|
| Serp-1 + CsA | Serp-1 100 ng/g IV POD (0-10), CsA 0.5 mg/kg/day | 13, >36, >36, 49, >110, >111, >112, >112 | >73 |
| CsA | 0.5 mg/kg/day | 10, 27, 31, 31, 32, 42, 44, 51 | 33.5 |
| Serp-1 + CsA | Serp-1 100 ng/g IV POD (0-10) CsA 0.25 mg/kg/day | 22, 23, 23, 24, >28, >29, >31, >31 | >26.25 |
| CsA | 0.25 mg/kg/day | 10, >10, >11, >11, 14, 15, 15, 17 | 12.88 |

What is claimed is:

1. A method of improving the transplantation outcome in a mammalian organ transplant recipient, said method comprising administering to said mammalian organ transplant recipient a therapeutically effective amount of a first agent, said first agent comprising mature, processed SERP-1, and a second agent, said second agent consisting of an immunosuppressive agent, wherein said second agent is an agent which acts synergistically with said first agent to improve said transplantation outcome.

2. The method of claim 1, wherein said mature, processed SERP-1 comprises the mature, processed form of a polypeptide having the amino acid sequence of SEQ ID NO: 1.

3. The method of claim 2, wherein said mature, processed SERP-1 consists of the mature, processed form of a polypeptide having the amino acid sequence of SEQ ID NO: 1.

4. The method of claim 3, wherein said first agent consists of said mature, processed SERP-1.

5. The method of claim 1, wherein said improvement in transplantation outcome is reduced graft rejection.

6. The method of claim 5, wherein said mature, processed SERP-1 comprises the mature, processed form of a polypeptide having the amino acid sequence of SEQ ID NO: 1.

7. The method of claim 6, wherein said mature, processed SERP-1 consists of the mature, processed form of a polypeptide having the amino acid sequence of SEQ ID NO: 1.

8. The method of claim 7, wherein said first agent consists of said mature, processed SERP-1.

9. The method of claim 5, wherein said reduced graft rejection is reduced chronic graft rejection.

10. The method of claim 9, wherein said mature, processed SERP-1 comprises the mature, processed form of a polypeptide having the amino acid sequence of SEQ ID NO: 1.

11. The method of claim 10, wherein said mature, processed SERP-1 consists of the mature, processed form of a polypeptide having the amino acid sequence of SEQ ID NO: 1.

12. The method of claim 11, wherein said first agent consists of said mature, processed SERP-1.

13. The method of claim 5, wherein said reduced graft rejection is reduced acute graft rejection.

14. The method of claim 13, wherein said mature, processed SERP-1 comprises the mature, processed form of a polypeptide having the amino acid sequence of SEQ ID NO: 1.

15. The method of claim 14, wherein said mature, processed SERP-1 consists of the mature, processed form of a polypeptide having the amino acid sequence of SEQ ID NO: 1.

16. The method of claim 15, wherein said first agent consists of said mature, processed SERP-1.

17. The method of claim 1, wherein said organ transplant is an allograft.

18. The method of claim 17, wherein said mature, processed SERP-1 comprises the mature, processed form of a polypeptide having the amino acid sequence of SEQ ID NO: 1.

19. The method of claim 1, wherein said organ transplant is a xenograft.

20. The method of claim 19, wherein said mature, processed SERP-1 comprises the mature, processed form of a polypeptide having the amino acid sequence of SEQ ID NO: 1.

21. The method of claim 1, wherein said mammalian organ transplant recipient is human.

22. The method of claim 21, wherein said mature, processed SERP-1 comprises the mature, processed form of a polypeptide having the amino acid sequence of SEQ ID NO: 1.

23. The method of claim 1, wherein said second agent suppresses T or B cell activity.

24. The method of claim 23, wherein said mature, processed SERP-1 comprises the mature, processed form of a polypeptide having the amino acid sequence of SEQ ID NO: 1.

25. The method of claim 23, wherein said second agent suppresses T and B cell activity.

26. The method of claim 25, wherein said mature, processed SERP-1 comprises the mature, processed form of a polypeptide having the amino acid sequence of SEQ ID NO: 1.

27. The method of claim 23, wherein said second agent suppresses T cell activity.

28. The method of claim 27, wherein said mature, processed SERP-1 comprises the mature, processed form of a polypeptide having the amino acid sequence of SEQ ID NO: 1.

29. The method of claim 23, wherein said second agent suppresses B cell activity.

30. The method of claim 29, wherein said mature, processed SERP-1 comprises the mature, processed form of a polypeptide having the amino acid sequence of SEQ ID NO: 1.

31. The method of claim 1, wherein said first agent suppresses the activity of an early regulatory inflammatory component.

32. The method of claim 31, wherein said mature, processed SERP-1 comprises the mature, processed form of a polypeptide having the amino acid sequence of SEQ ID NO: 1.

33. The method of claim 31, wherein said early regulatory inflammatory component is neutrophils, monocytes, macrophages, or natural killer (NK) cells.

34. The method of claim 33, wherein said mature, processed SERP-1 comprises the mature, processed form of a polypeptide having the amino acid sequence of SEQ ID NO: 1.

35. The method of claim 1, wherein said first agent reduces mononuclear cell invasion or transplant vasculopathy.

36. The method of claim 35, wherein said mature, processed SERP-1 comprises the mature, processed form of a polypeptide having the amino acid sequence of SEQ ID NO: 1.

37. The method of claim 1, wherein said therapeutically effective amount of said first agent is about 1 pg/kg to about 1 g/kg and said therapeutically effective amount of said second agent is about 1 mg/kg to about 20 mg/kg.

38. The method of claim 37, wherein said mature, processed SERP-1 comprises the mature, processed form of a polypeptide having the amino acid sequence of SEQ ID NO: 1.

39. The method of claim 38, wherein said mature, processed SERP-1 consists of the mature, processed form of a polypeptide having the amino acid sequence of SEQ ID NO: 1.

40. The method of claim 39, wherein said first agent consists of said mature, processed SERP-1.

41. The method of claim 37, wherein said therapeutically effective amount of said first agent is about 3 µg/kg to about 1 mg/kg.

42. The method of claim 41, wherein said mature, processed SERP-1 comprises the mature, processed form of a polypeptide having the amino acid sequence of SEQ ID NO: 1.

43. The method of claim 41, wherein said therapeutically effective amount of said first agent is about 3 µg/kg to 10 µg/kg.

44. The method of claim 43, wherein said mature, processed SERP-1 comprises the mature, processed form of a polypeptide having the amino acid sequence of SEQ ID NO: 1.

45. The method of claim 41, wherein said therapeutically effective amount of said first agent is 10 µg/kg to 100 µg/kg.

46. The method of claim 45, wherein said mature, processed SERP-1 comprises the mature, processed form of a polypeptide having the amino acid sequence of SEQ ID NO: 1.

47. The method of claim 41, wherein said therapeutically effective amount of said first agent is 100 µg/kg to about 1 mg/kg.

48. The method of claim 47, wherein said mature, processed SERP-1 comprises the mature, processed form of a polypeptide having the amino acid sequence of SEQ ID NO: 1.

49. The method of claim 1, wherein said therapeutically effective amount of said first agent is about 1 pg/kg to about 1 g/kg and said therapeutically effective amount of said second agent is 0.25 mg/kg to 1 mg/kg, wherein said immunosuppressive agent is cyclosporin A.

50. The method of claim 49, wherein said mature, processed SERP-1 comprises the mature, processed form of a polypeptide having the amino acid sequence of SEQ ID NO: 1.

51. The method of claim 1, wherein said therapeutically effective amount of said second agent is reduced as compared to a therapeutically effective amount of said second agent alone.

52. The method of claim 51, wherein said mature, processed SERP-1 comprises the mature, processed form of a polypeptide having the amino acid sequence of SEQ ID NO: 1.

53. The method of claim 51, wherein said immunosuppressive agent is cyclosporin A.

54. The method of claim 53, wherein said mature, processed SERP-1 comprises the mature, processed form of a polypeptide having the amino acid sequence of SEQ ID NO: 1.

55. The method of claim 1, wherein said immunosuppressive agent is a cyclic peptide produced by the fungus species *Tolypocladium Inflatum Gams*.

56. The method of claim 55, wherein said mature, processed SERP-1 comprises the mature, processed form of a polypeptide having the amino acid sequence of SEQ ID NO: 1.

57. The method of claim 55, wherein said immunosuppressive agent is cyclosporin A.

58. The method of claim 57, wherein said mature, processed SERF-1 comprises the mature, processed form of a polypeptide having the amino acid sequence of SEQ ID NO: 1.

59. The method of claim 1, wherein said improvement in transplantation outcome is increased graft survival.

60. The method of claim 59, wherein said mature, processed SERP-1 comprises the mature, processed form of a polypeptide having the amino acid sequence of SEQ ID NO: 1.

61. The method of claim 1, wherein said improvement in transplantation outcome is decreased lymphocytic infiltration, vasculitis, infarction, ischemia, thrombosis, intimal thickening, glomerular atrophy, glomerular sclerosis, tubular atrophy, hyalinization, interstitial fibrosis, cortical fibrosis, serum creatinine levels, intimal proliferation, hypertrophy, cardiac vessel disease post-transplant, graft intimal hyperplasia, luminal occlusion, or bronchitis obliterans.

62. The method of claim 61, wherein said mature, processed SERP-1 comprises the mature, processed form of a polypeptide having the amino acid sequence of SEQ ID NO: 1.

63. The method of claim 1, wherein said organ is a kidney.

64. The method of claim 63, wherein said mature, processed SERP-1 comprises the mature, processed form of a polypeptide having the amino acid sequence of SEQ ID NO: 1.

65. The method of claim 63, wherein said improvement in transplantation outcome is increased graft survival.

66. The method of claim 65, wherein said mature, processed SERP-1 comprises the mature, processed form of a polypeptide having the amino acid sequence of SEQ ID NO: 1.

67. The method of claim 63, wherein said improvement in transplantation outcome is decreased lymphocyte infiltration, intimal thickening, glomerular atrophy, glomerular sclerosis, tubular atrophy, hyalinization, interstitial fibrosis, cortical fibrosis, or serum creatinine levels.

68. The method of claim 67, wherein said mature, processed SERP-1 comprises the mature, processed form of a polypeptide having the amino acid sequence of SEQ ID NO: 1.

69. The method of claim 1, wherein said organ is a heart.

70. The method of claim 69, wherein said mature, processed SERP-1 comprises the mature, processed form of a polypeptide having the amino acid sequence of SEQ ID NO: 1.

71. The method of claim 69, wherein said improvement in transplantation outcome is increased graft survival.

72. The method of claim 71, wherein said mature, processed SERP-1 comprises the mature, processed form of a polypeptide having the amino acid sequence of SEQ ID NO: 1.

73. The method of claim 69, wherein said improvement in transplantation outcome is decreased intimal proliferation, hypertrophy, cardiac vessel disease post-transplant, graft intimal hyperplasia, or luminal occlusion.

74. The method of claim 73, wherein said mature, processed SERP-1 comprises the mature, processed form of a polypeptide having the amino acid sequence of SEQ ID NO: 1.

75. The method of claim 1, wherein said first agent and said second agent are co-administered.

76. The method of claim 75, wherein said mature, processed SERP-1 comprises the mature, processed form of a polypeptide having the amino acid sequence of SEQ ID NO: 1.

77. The method of claim 75, wherein said first agent and said second agent are co-administered for a period of about 1 to about 30 days post-transplant.

78. The method of claim 77, wherein said mature, processed SERP-1 comprises the mature, processed form of a polypeptide having the amino acid sequence of SEQ ID NO: 1.

79. The method of claim 77, wherein said first agent and said second agent are co-administered for a period of about 8 to about 15 days post-transplant.

80. The method of claim 79, wherein said mature, processed SERP-1 comprises the mature, processed form of a polypeptide having the amino acid sequence of SEQ ID NO: 1.

81. The method of claim 75, wherein said first agent and said second agent are co-administered over a sequential period of days.

82. The method of claim 81, wherein said mature, processed SERP-1 comprises the mature, processed form of a polypeptide having the amino acid sequence of SEQ ID NO: 1.

83. The method of claim 1, wherein said second agent is administered prior to said first agent.

84. The method of claim 83, wherein said mature, processed SERP-1 comprises the mature, processed form of a polypeptide having the amino acid sequence of SEQ ID NO: 1.

85. The method of claim 83, wherein said second agent is administered from about 1 to about 30 days prior to said first agent.

86. The method of claim 85, wherein said mature, processed SERP-1 comprises the mature, processed form of a polypeptide having the amino acid sequence of SEQ ID NO: 1.

87. The method of claim 1, wherein said first agent or said second agent is administered by parenteral administration.

88. The method of claim 87, wherein said mature, processed SERP-1 comprises the mature, processed form of a polypeptide having the amino acid sequence of SEQ ID NO: 1.

89. The method of claim 87, wherein said parenteral administration is intravascular, intravenous, intra-arterial, subcutaneous, intramuscular, intraperitoneal, intraventricular, or intraepidural administration.

90. The method of claim 89, wherein said mature, processed SERP-1 comprises the mature, processed form of a polypeptide having the amino acid sequence of SEQ ID NO: 1.

91. The method of claim 1, wherein said first agent or said second agent is topically administered.

92. The method of claim 1, wherein said first agent or said second agent is administered in a sustained-release formulation.

93. The method of claim 92, wherein said sustained-release formulation is administered by depot injection or by erodible implant.

94. The method of claim 1, wherein said immunosuppressive agent is cyclosporin A.

95. The method of claim 94, wherein said mature, processed SERP-1 comprises the mature, processed form of a polypeptide having the amino acid sequence of SEQ ID NO: 1.

96. The method of claim 95, wherein said mature, processed SERP-1 consists of the mature, processed form of a polypeptide having the amino acid sequence of SEQ ID NO: 1.

97. The method of claim 96, wherein said first agent consists of said mature, processed SERP-1.

98. The method of claim 1, wherein said immunosuppressive agent is rapamycin.

99. The method of claim 98, wherein said mature, processed SERP-1 comprises the mature, processed form of a polypeptide having the amino acid sequence of SEQ ID NO: 1.

100. The method of claim 1, wherein said immunosuppressive agent is FK501.

101. The method of claim 100, wherein said mature, processed SERP-1 comprises the mature, processed form of a polypeptide having the amino acid sequence of SEQ ID NO: 1.

102. The method of claim 1, wherein said immunosuppressive agent is mycophenolate mofetil.

103. The method of claim 92, wherein said mature, processed SERF-1 comprises the mature, processed form of a polypeptide having the amino acid sequence of SEQ ID NO: 1.

104. The method of claim 1, wherein said immunosuppressive agent is azathioprine.

105. The method of claim 104, wherein said mature, processed SERP-1 comprises the mature, processed form of a polypeptide having the amino acid sequence of SEQ ID NO: 1.

106. The method of claim 1, wherein said immunosuppressive agent is deoxyspergualin.

107. The method of claim 106, wherein said mature, processed SERP-1 comprises the mature, processed form of a polypeptide having the amino acid sequence of SEQ ID NO: 1.

108. The method of claim 1, wherein said immunosuppressive agent is FK506.

109. The method of claim 108, wherein said mature, processed SERP-1 comprises the mature, processed form of a polypeptide having the amino acid sequence of SEQ ID NO: 1.

* * * * *

SEQUENCE LISTING

<160> NUMBER OF SEQ ID NOS: 1

<210> SEQ ID NO 1
<211> LENGTH: 369
<212> TYPE: PRT
<213> ORGANISM: Myxoma virus

<400> SEQUENCE: 1

-continued

```
Met Lys Tyr Leu Val Leu Val Leu Cys Leu Thr Ser Cys Ala Cys Arg
1               5                   10                  15

Asp Ile Gly Leu Trp Thr Phe Arg Tyr Val Tyr Asn Glu Ser Asp Asn
            20                  25                  30

Val Val Phe Ser Pro Tyr Gly Leu Thr Ser Ala Leu Ser Val Leu Arg
        35                  40                  45

Ile Ala Ala Gly Gly Asn Thr Lys Arg Glu Ile Asp Val Pro Glu Ser
    50                  55                  60

Val Val Glu Asp Ser Asp Ala Phe Leu Ala Leu Arg Glu Leu Phe Val
65                  70                  75                  80

Asp Ala Ser Val Pro Leu Arg Pro Glu Phe Thr Ala Glu Phe Ser Ser
                85                  90                  95

Arg Phe Asn Thr Ser Val Gln Arg Val Thr Phe Asn Ser Glu Asn Val
            100                 105                 110

Lys Asp Val Ile Asn Ser Tyr Val Lys Asp Lys Thr Gly Gly Asp Val
        115                 120                 125

Pro Arg Val Leu Asp Ala Ser Leu Asp Arg Asp Thr Lys Met Leu Leu
    130                 135                 140

Leu Ser Ser Val Arg Met Lys Thr Ser Trp Arg His Val Phe Asp Pro
145                 150                 155                 160

Ser Phe Thr Thr Asp Gln Pro Phe Tyr Ser Gly Asn Val Thr Tyr Lys
                165                 170                 175

Val Arg Met Met Asn Lys Ile Asp Thr Leu Lys Thr Glu Thr Phe Thr
            180                 185                 190

Leu Arg Asn Val Gly Tyr Ser Val Thr Glu Leu Pro Tyr Lys Arg Arg
        195                 200                 205

Gln Thr Ala Met Leu Leu Val Val Pro Asp Asp Leu Gly Glu Ile Val
    210                 215                 220

Arg Ala Leu Asp Leu Ser Leu Val Arg Phe Trp Ile Arg Asn Met Arg
225                 230                 235                 240

Lys Asp Val Cys Gln Val Val Met Pro Lys Phe Ser Val Glu Ser Val
                245                 250                 255

Leu Asp Leu Arg Asp Ala Leu Gln Arg Leu Gly Val Arg Asp Ala Phe
            260                 265                 270

Asp Pro Ser Arg Ala Asp Phe Gly Gln Ala Ser Pro Ser Asn Asp Leu
        275                 280                 285

Tyr Val Thr Lys Val Leu Gln Thr Ser Lys Ile Glu Ala Asp Glu Arg
    290                 295                 300

Gly Thr Thr Ala Ser Ser Asp Thr Ala Ile Thr Leu Ile Pro Arg Asn
305                 310                 315                 320

Ala Leu Thr Ala Ile Val Ala Asn Lys Pro Phe Met Phe Leu Ile Tyr
                325                 330                 335

His Lys Pro Thr Thr Thr Val Leu Phe Met Gly Thr Ile Thr Lys Gly
            340                 345                 350

Glu Lys Val Ile Tyr Asp Thr Glu Gly Arg Asp Asp Val Val Ser Ser
        355                 360                 365

Val
```